(12) United States Patent
Onobori

(10) Patent No.: US 11,559,194 B2
(45) Date of Patent: Jan. 24, 2023

(54) ENDOSCOPE LIGHT SOURCE DEVICE AND ENDOSCOPE SYSTEM

(71) Applicant: HOYA CORPORATION, Tokyo (JP)

(72) Inventor: Kunihiko Onobori, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 170 days.

(21) Appl. No.: 16/623,607

(22) PCT Filed: Aug. 28, 2018

(86) PCT No.: PCT/JP2018/031686
§ 371 (c)(1),
(2) Date: Dec. 17, 2019

(87) PCT Pub. No.: WO2019/044802
PCT Pub. Date: Mar. 7, 2019

(65) Prior Publication Data
US 2020/0205648 A1     Jul. 2, 2020

(30) Foreign Application Priority Data
Aug. 28, 2017 (JP) .............................. JP2017-163219

(51) Int. Cl.
*A61B 1/06* (2006.01)
*A61B 1/00* (2006.01)
(Continued)

(52) U.S. Cl.
CPC ........ *A61B 1/0638* (2013.01); *A61B 1/00006* (2013.01); *A61B 1/0669* (2013.01);
(Continued)

(58) Field of Classification Search
CPC . A61B 1/0684; A61B 1/0638; A61B 1/00006; A61B 1/0669; A61B 1/07; H05B 45/20; H05B 45/10; G02B 23/26
See application file for complete search history.

(56) References Cited

U.S. PATENT DOCUMENTS

2002/0062061 A1* 5/2002 Kaneko ................. A61B 1/045
600/118
2003/0201451 A1 10/2003 Suehiro et al.
(Continued)

FOREIGN PATENT DOCUMENTS

| EP | 3 111 822 | 1/2017 |
|---|---|---|
| EP | 3 295 861 | 3/2018 |

(Continued)

OTHER PUBLICATIONS

International Search Report issued in International Patent Application No. PCT/JP2018/031686, dated Nov. 13, 2018, along with an English translation thereof.
(Continued)

*Primary Examiner* — Anh Tuan T Nguyen
*Assistant Examiner* — Shankar Raj Ghimire
(74) *Attorney, Agent, or Firm* — Greenblum & Bernstein, P.L.C.

(57) ABSTRACT

A light source device includes: a first optical element that generates transmitted light obtained by removing a first wavelength band component from incident light and generates reflected light obtained by extracting the first wavelength band component from the incident light; a first light source that emits light that includes at least a component of the first wavelength band and that causes the light to be incident on the first optical element so as to be reflected light of the first optical element; a second light source that emits light so that light including a component of a wide second wavelength band including the first wavelength band to be transmitted light of the first optical element; and a control unit that controls driving of the first light source and the second light source. The control unit controls on/off of emission of the first and second light source emission light.

4 Claims, 15 Drawing Sheets

(51) Int. Cl.
    *H05B 45/10*       (2020.01)
    *A61B 1/07*        (2006.01)
(52) U.S. Cl.
    CPC ............... *A61B 1/07* (2013.01); *H05B 45/10* (2020.01); *A61B 1/0002* (2013.01); *A61B 1/0684* (2013.01)

(56) References Cited

U.S. PATENT DOCUMENTS

| | | | | |
|---|---|---|---|---|
| 2004/0144987 | A1* | 7/2004 | Ouderkirk | H01L 33/60 257/98 |
| 2007/0098028 | A1* | 5/2007 | Alcock | H01S 5/40 372/50.122 |
| 2008/0130285 | A1* | 6/2008 | Negley | F21S 6/005 362/257 |
| 2011/0032350 | A1* | 2/2011 | Kikuchi | A61B 1/0638 348/240.99 |
| 2013/0016305 | A1* | 1/2013 | Kaneda | G03B 21/006 372/29.014 |
| 2015/0228868 | A1* | 8/2015 | Ouderkirck | F21V 9/38 362/84 |
| 2016/0062103 | A1* | 3/2016 | Yang | A61B 1/042 250/552 |
| 2017/0020377 | A1* | 1/2017 | Takeuchi | A61B 1/043 |
| 2017/0156577 | A1* | 6/2017 | Machida | F21V 13/12 |
| 2017/0167919 | A1* | 6/2017 | Learmonth | G01J 3/0275 |
| 2018/0064321 | A1* | 3/2018 | Muramatsu | A61B 1/0669 |
| 2019/0117055 | A1* | 4/2019 | Ito | A61B 1/05 |
| 2019/0215925 | A1* | 7/2019 | Tanaka | G06T 11/001 |
| 2019/0282135 | A1* | 9/2019 | Ito | A61B 1/00006 |

FOREIGN PATENT DOCUMENTS

| | | |
|---|---|---|
| JP | 2003-298117 | 10/2003 |
| JP | 2009-206428 | 9/2009 |
| JP | 2011-188929 | 9/2011 |
| JP | 5198694 | 5/2013 |
| WO | 2015/156153 | 10/2015 |
| WO | 2016/185647 | 11/2016 |
| WO | 2016/189892 A1 | 12/2016 |

OTHER PUBLICATIONS

International Preliminary Report of Patentability issued in International Patent Application No. PCT/JP2018/031686, dated Mar. 3, 2020, along with an English translation thereof.

Japanese Office Action, Japanese Patent Office, Application No. 2019-539513, dated Jan. 19, 2021.

* cited by examiner

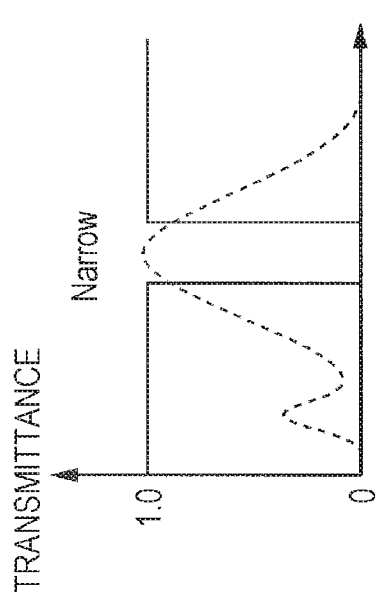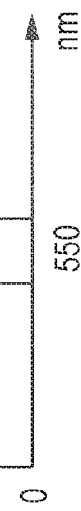
FIG. 8 (a)
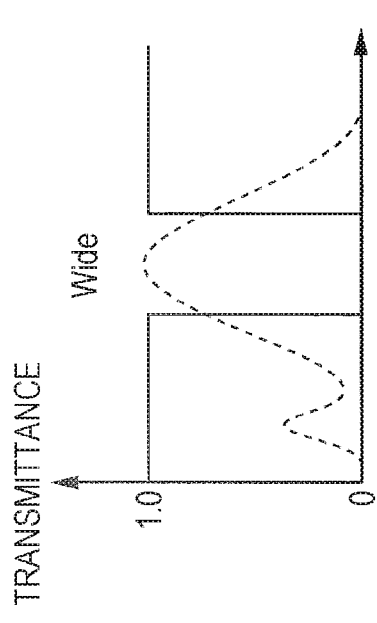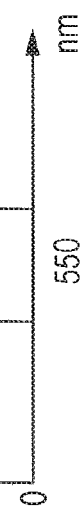
FIG. 8 (b)

ENDOSCOPE LIGHT SOURCE DEVICE AND ENDOSCOPE SYSTEM

TECHNICAL FIELD

The present invention relates to an endoscope light source device and an endoscope system.

BACKGROUND ART

There is a conventionally known endoscope system that acquires an image and information of a biological tissue imaged by an endoscope and performs diagnosis. In order to obtain an image that enhances a special portion in a biological tissue in the diagnosis using an endoscope system, a special ray of light in a specific wavelength band different from white light being normal light is used as illumination light for the biological tissue. For example, an image that enhances a portion of a blood vessel in a biological tissue is acquired, or information regarding a biological substance in the biological tissue, for example, the concentration of hemoglobin and the oxygen saturation of hemoglobin is acquired.

There is known a light source device used for an endoscope system capable of capturing a special image using such a special ray of light, that is, a special ray of light having a spectral intensity characteristic different from that of white light (Patent Literature 1).

The known light source device includes a light source device including two light emitting diodes (LEDs) and a rotating optical filter. One of the two LEDs is a purple LED that emits light in the purple wavelength band. The other LED is a phosphor based LED having a blue LED and a yellow phosphor, and mixes blue LED light and yellow fluorescence to emit pseudo white light. The optical filter is a wavelength selection filter that allows passage of only light in a wavelength band having high absorbance with respect to a specific biological tissue, and can be inserted into and extracted from an optical path of light emitted from the phosphorbased LED.

When the optical filter is removed from the optical path in the light source device, the light emitted from the phosphorbased LED illuminates an object as white light (normal light) with no limitation of the wavelength band. In contrast, when the optical filter is inserted on the optical path, both the irradiation light emitted from the phosphor-based LED and having wavelength band limitation and the irradiation light emitted from the purple LED illuminate the object as a special ray of light. In this manner, with the spectral intensity characteristic of illumination light different from the characteristic of white light and allowing only the light of a specific wavelength band to illuminate the object, it is possible to capture an image in which a specific tissue is enhanced from among biological tissue objects.

CITATION LIST

Patent Literature

Patent Literature 1: JP 5198694 B2

SUMMARY OF INVENTION

Technical Problem

However, since the known light source device uses a rotating optical filter, there would be a need to obtain a rotation detection signal or an optical filter position detection signal to indicate the rotation state of the optical filter by a sensor or the like, and a need to control the light source device corresponding to the rotation. In addition, there would be a need to perform rotation control for setting the rotation speed of the optical filter to a predetermined speed, complicating the control of the light source device.

Therefore, the light source device preferably has a configuration capable of repeatedly switching and emitting a special ray of light and normal light such as white light without using a rotating optical filter.

In view of this, the present invention aims to provide an endoscope light source device and an endoscope system that can easily switch special rays of light as illumination light of an object without using a rotating optical filter that is used in a conventional light source device.

Solution to Problem

One aspect of the present invention is an endoscope light source device configured to emit at least one of first light and second light in a wide second wavelength band including a first wavelength band of the first light. The light source device includes:

a first optical element configured such that first optical path incident light that is incident from a first optical path is changed to first optical path passing light by extracting a light component of the first wavelength band and removing light components other than the first wavelength band from the first optical path incident light, second optical path incident light that is incident from a second optical path of the optical element is changed to second optical path passing light by removing the light component of the first wavelength band and extracting the light components other than the light component of the first wavelength band from the second optical path incident light, and an emission optical path of the first optical path passing light and an emission optical path of the second optical path passing light are overlapped and light that passes through the overlapped emission optical paths is to be emitted;

a first light source configured to emit first light source emission light that includes at least the light component of the first wavelength band and to allow the first light source emission light to be incident on the first optical element so that the first light source emission light is the first optical path incident light;

a second light source configured to emit second light source emission light that includes at least a light component of the second wavelength band and to allow light obtained from the second light source emission light and including at least the light component of the second wavelength band to be the second optical path incident light of the first optical element; and a control unit configured to control on/off of emission of the first light source emission light and emission of the second light source emission light to perform emission of the first light and emission of the second light selectively.

It is preferable that the control unit is configured to control driving of the first light source and the second light source so as to turn on emission of the first light source emission light and emission of the second light source emission light to generate the second light, and turn on emission of the first light source emission light and turn off emission of the second light source emission light to generate the first light.

According to an embodiment, it is preferable to include a second optical element configured to generate emission light to be emitted to the first optical element so as to be the second optical path incident light of the first optical element in response to incidence of the second light source emission light.

According to an embodiment, it is preferable that a wavelength band of the first light source emission light and a wavelength band of the second light source emission light are identical each other.

According to an embodiment, it is preferable that the control unit controls the first light source light so that light intensity of the first light source emission light when the first light is emitted is different from the light intensity of the first light source emission light when the second light is emitted.

According to an embodiment, it is preferable that the endoscope light source device includes a third light source configured to emit third light source emission light having a peak wavelength longer than a peak wavelength of the first light and a peak wavelength of the second light, toward the second optical element, and that the second optical element is configured to emit combined light of the third light source emission light and light that includes at least a light component of the second wavelength band of the second light source emission light, to the first optical element in response to incidence of the third light source emission light and the second light source emission light.

At this time, according to an embodiment, it is preferable that the endoscope light source device includes:

a fourth light source that emits fourth light source emission light of a wavelength band having a peak wavelength shorter than the peak wavelength of the first light and the peak wavelength of the second light and including a wavelength of 415 nm; and a third optical element configured to emit combined light of the fourth light source emission light and the emission light from the first optical element, as third light, in response to incidence of the fourth light source emission light and the emission light from the first optical element.

According to an embodiment, it is preferable that the endoscope light source device includes a fourth light source configured to emit fourth light source emission light of a wavelength band having a peak wavelength shorter than the peak wavelength of the first light and the peak wavelength of the second light and including a wavelength of 415 nm and that the second optical element is configured to emit combined light of the fourth light source emission light and light that includes at least a light component of the second wavelength band of the second light source emission light, to the first optical element in response to incidence of the fourth light source emission light and the second light source emission light.

At this time, according to an embodiment, it is preferable that the endoscope light source device includes:

a third light source configured to emit third light source emission light having a peak wavelength longer than the peak wavelength of the first light and the peak wavelength of the second light; and a third optical element configured to emit the third light source emission light and combined light by the first optical element, as third light, in response to incidence of the third light source emission light and the emission light from the first optical element.

According to an embodiment, it is preferable that the control unit is configured to control driving of the first light source, the second light source, the third light source, and the fourth light source so as to repeatedly emit the first light, the second light, and the third light, as emission light.

According to an embodiment, it is preferable that the first light source includes: a first solid-state light emitting element that emits first excitation light; and a first phosphor that emits first fluorescence by the first excitation light, and that the first light source emission light includes the first excitation light and the first fluorescence.

According to an embodiment, it is preferable that the first wavelength band is included in the wavelength band of the first fluorescence.

According to an embodiment, it is preferable that the first light source includes a first reflection surface so as to cover a portion of a space around a light emission surface of the first light source so that a portion of the first excitation light that has passed without energizing the first phosphor is reflected to irradiate the first phosphor to increase intensity of the first fluorescence emitted from the first phosphor.

According to an embodiment, it is preferable that the first optical path emission light is reflected light reflected by a surface of the first optical element, and that the second optical path emission light is transmitted light that has transmitted through an inside of the first optical element.

According to an embodiment, it is preferable that the second light source includes: a second solid-state light emitting element that emits second excitation light; and a second phosphor that emits second fluorescence by the second excitation light, and that the second light source emission light includes the second excitation light and the second fluorescence.

According to an embodiment, it is preferable that the second wavelength band is included in the wavelength band of the second fluorescence.

Furthermore, according to an embodiment, it is preferable that the second light source includes a second reflection surface so as to cover a portion of a space around a light emission surface of the second light source so that a portion of the second excitation light that has passed without energizing the second phosphor is reflected to irradiate the second phosphor to increase intensity of the second fluorescence emitted from the second phosphor.

Another aspect of the present invention is an endoscope system including:

the endoscope light source device;

an endoscope that uses at least the first light and the second light emitted from the endoscope light source device as illumination light of an object.

Advantageous Effects of Invention

According to the above-described endoscope light source device for an endoscope, it is possible to easily switch special rays of light as illumination light of an object without using a rotating optical filter as in a conventional light source device.

BRIEF DESCRIPTION OF DRAWINGS

FIGS. 8(a) and 8(b) are diagrams illustrating an example of characteristics of transmittance in transmitted light and reflectance in reflected light of an optical element used in an embodiment.

DESCRIPTION OF EMBODIMENTS

Hereinafter, an endoscope light source device and an endoscope system according to the present invention will be described with reference to the drawings.

Figure 1:
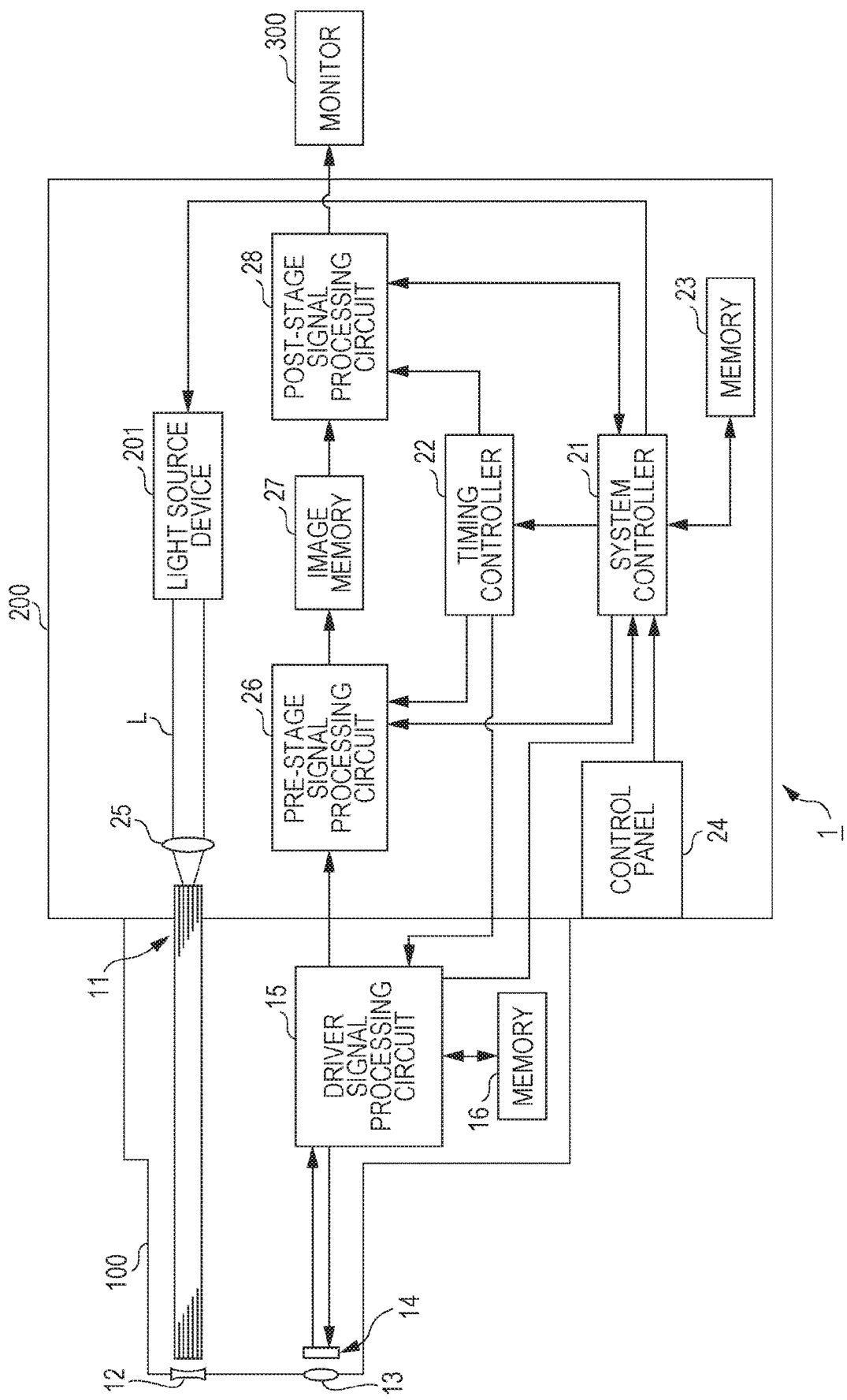
FIG. 1 is a block diagram illustrating a configuration of an endoscope system according to an embodiment.

FIG. 1 is a block diagram illustrating a configuration of an endoscope system including an endoscope light source device. An endoscope system 1 illustrated in FIG. 1 is a system specialized for medical use, and includes an electronic scope (endoscope) 100, a processor 200, and a monitor 300.

The processor 200 includes a system controller 21 and a timing controller 22. The system controller 21 executes various programs stored in the memory 23 and integrally controls the entire electronic endoscope system 1. The system controller 21 is connected to an operation panel 24. The system controller 21 changes each of operation of the electronic endoscope system 1 and parameters for each of the operation in accordance with an operator's instruction input to the operation panel 24. The operator's input instruction includes, for example, an instruction to switch an observation mode of the electronic endoscope system 1. The observation mode includes a normal observation mode and a special observation mode. Details of each of the observation modes will be described below. The timing controller 22 outputs a clock pulse for adjusting the operation timing of individual units to individual circuits in the electronic endoscope system 1.

Figure 5:
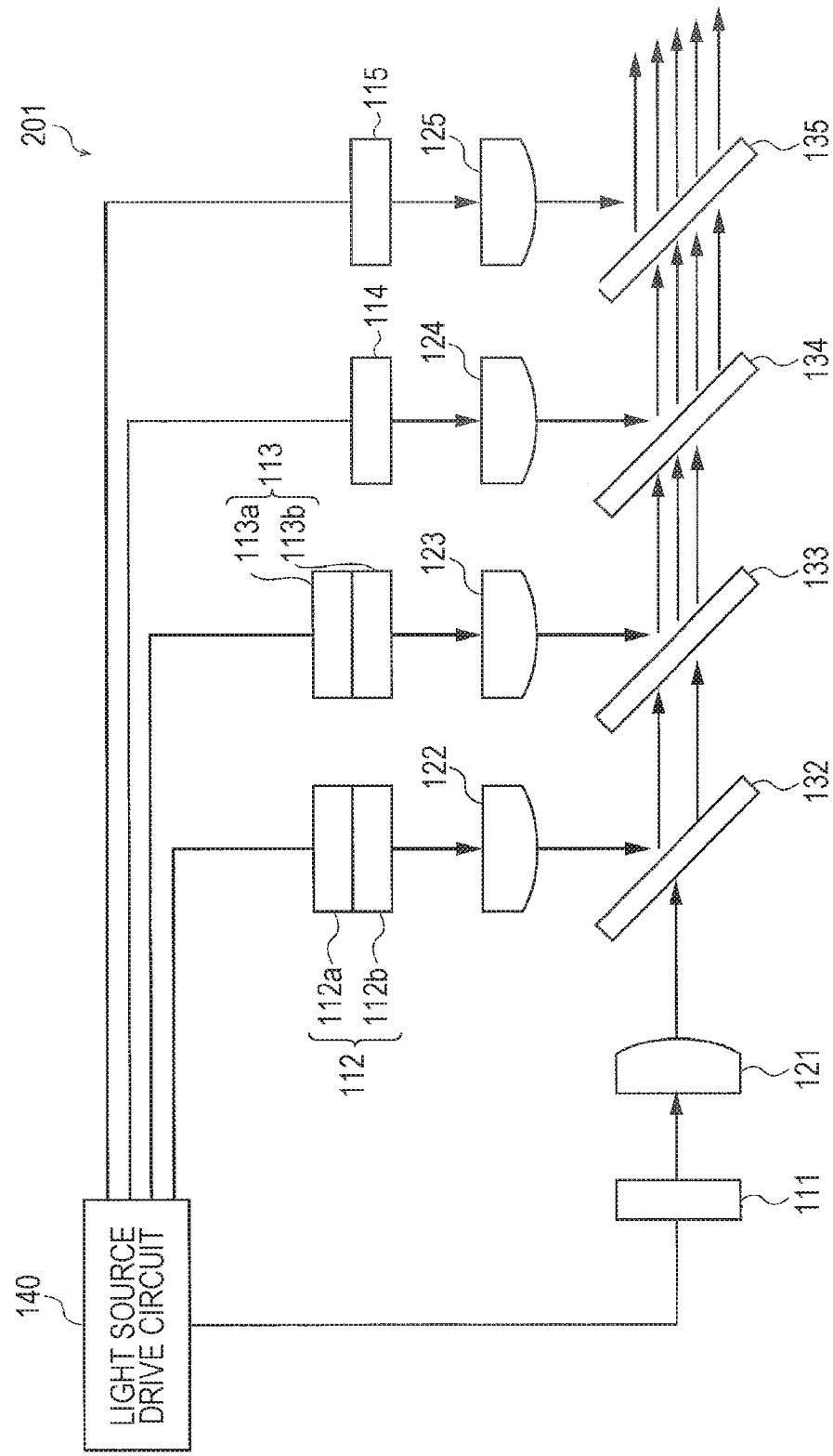
FIG. 5 is a diagram illustrating a configuration of an endoscope light source device according to an embodiment.

The processor 200 includes a light source device 201. The light source device 201 includes a first light source 111 to a fifth light source 115 and a light source drive circuit 140, as illustrated in FIG. 5 below. The first to fifth light sources 111 to 115 are individually controlled to emit light by the light source drive circuit 140. As a result, the light source device 201 emits irradiation light L.

In the embodiment illustrated in FIG. 1, the light source device 201 is provided in the processor 200. In another embodiment, however, the light source device 201 is a device separate from the processor 200 (more precisely, a part constituting an image processing device).

The light source device 201 will be described below.

As illustrated in FIG. 1, the irradiation light L emitted from the light source device 201 is focused by the condenser lens 25 onto an incident end face of a Light Carrying Bundle (LCB) 11 to be incident on the LCB 11.

The irradiation light L incident on the LCB 11 propagates within the LCB 11. The irradiation light L propagating through the LCB 11 is emitted from an exit end surface of the LCB 11 disposed at a distal end of the electronic scope 100 so as to be directed to the object via a light distribution lens 12 to illuminate the object. Return light from the object irradiated with the irradiation light L from the light distribution lens 12 forms an optical image on a light receiving surface of the solid-state image sensor 14 via an objective lens 13.

The solid-state image sensor 14 is a single-plate color Charge Coupled Device (CCD) image sensor having a Bayer pixel arrangement. The solid-state image sensor 14 stores an optical image formed by each of pixels on the light receiving surface, as a charge corresponding to the amount of light, and generates and outputs image signals of Red (R), Green (G), and Blue (B). Note that the solid-state image sensor 14 is not limited to a CCD image sensor, and may be replaced with a Complementary Metal Oxide Semiconductor (CMOS) image sensor or other types of imaging devices. The solid-state image sensor 14 may include a complementary color filter.

The electronic scope 100 includes a driver signal processing circuit 15 provided in the connection portion thereof. An image signal of an object irradiated with light from the light distribution lens 12 is input to the driver signal processing circuit 15 from the solid-state image sensor 14 at a frame period. The frame period is 1/30 seconds, for example. The driver signal processing circuit 15 performs predetermined processing on the image signal input from the solid-state image sensor 14 and outputs the processed image signal to a pre-stage signal processing circuit 26 of the processor 200.

The driver signal processing circuit 15 also accesses memory 16 and reads out device-specific information of the electronic scope 100. The device-specific information of the electronic scope 100 recorded in the memory 16 includes, for example, the number of pixels and sensitivity of the solid-state image sensor 14, an operable frame rate, a model number, or the like. The driver signal processing circuit 15 outputs the device-specific information read from the memory 16 to the system controller 21.

The system controller 21 performs various calculations based on the device-specific information of the electronic scope 100 and generates a control signal. The system controller 21 controls the operation and timing of various circuits in the processor 200 using the generated control signal so as to perform processing suitable for the electronic scope 100 connected to the processor 200.

The timing controller 22 supplies a clock pulse to the driver signal processing circuit 15 in accordance with timing control by the system controller 21. The driver signal processing circuit 15 performs driving control of the solid-state image sensor 14 at a timing synchronized with the frame rate of the video image processed on the processor 200 side in accordance with the clock pulse supplied from the timing controller 22.

The pre-stage signal processing circuit 26 performs predetermined signal processing such as demosaic processing, matrix calculation, and YIC separation on the image signal input from the driver signal processing circuit 15 in one frame period, and outputs the processed signal to the image memory 27.

The image memory 27 buffers the image signal input from the pre-stage signal processing circuit 26 and outputs the signal to a poet-stage signal processing circuit 28 in accordance with the timing control by the timing controller 22.

The poet-stage signal processing circuit 28 processes the image signal input from the image memory 27 to generate monitor display screen data, and converts the generated monitor display screen data into a predetermined video format signal. The converted video format signal is output to the monitor 300. With this processing, an image of the object is displayed on a display screen of the monitor 300.

The endoscope system 1 has a plurality of observation modes including a normal observation mode and a special observation mode for observing an object. Each of observation modes is switched manually or automatically depending on the object to be observed. For example, when it is desired to observe the object with illumination with normal light, the observation mode is switched to the normal observation mode. An example of the normal light is white light. White light includes pseudo white light containing a mixture of light of a plurality of wavelength bands and having non-flat spectral intensity distribution, in addition to light having a flat spectral intensity distribution in the visible light band. In another case, for example, where it is desired to obtain a captured image in which a specific biological tissue is enhanced by illuminating the object with a special ray of light, the observation mode is switched to the special observation mode by an operation through the operation panel 24.

The special observation mode includes: a special observation mode 1 capable of acquiring a narrow-band image suitable for clearly grasping the running state of blood vessels (blood vessels in each of layers such as the superficial layer, middle layer, and deep layer) difficult to observe in the normal observation mode; and a special observation mode 2 capable of quantitatively analyzing and imaging biological information such as oxygen saturation of the object. The special observation mode 2 is useful in that the presence or absence of a malignant tumor can be determined from the oxygen saturation information of the object obtained from the captured image of the object under illumination.

The illumination light of the object used in the special observation mode 1 is, for example, narrow-band light having a sharp peak at a specific wavelength, being light having high absorbance with respect to a specific biological tissue. Examples of the light of a specific wavelength include light in the vicinity of 415 nm (for example, 415±5 nm) having a high absorbance for superficial blood vessels, light in the vicinity of 550 nm (for example, 550±5 nm) with high absorbance for middle blood vessels deeper than the superficial layer, and light in the vicinity of 650 nm (for example, 650±5 nm) having high absorbance for deep blood vessels deeper than the middle layer. Note that the longer the wavelength, the deeper the degree of penetration into the biological tissue. For this reason, the degree of depth of penetration increases in the order of narrow-band light in the vicinity of 415 nm, 550 nm, and 650 nm. Hereinafter, a case where the biological tissue enhanced in the special observation mode is a superficial blood vessel will be mainly described.

Blood containing hemoglobin is circulated in the superficial blood vessels. Hemoglobin is known to have absorbance peaks in the vicinity of wavelengths of 415 nm and 550 nm. Accordingly, with emission of a special ray of light suitable for enhancing the superficial blood vessels (specifically, light having a higher intensity in the vicinity of the wavelength of 415 nm, which is the peak of hemoglobin absorbance than other wavelength bands) onto the object, it is possible to obtain a captured image in which the superficial blood vessels are enhanced. The special ray of light having a high intensity in the vicinity of the wavelength of 550 nm has a relatively high absorbance even for the superficial blood vessels. In other words, a high intensity special ray of light in the vicinity of the wavelength of 550 nm also contributes to the enhanced display of the superficial blood vessels. Therefore, with emission of a high intensity special ray of light in the vicinity of 550 nm, which is another peak of absorbance of hemoglobin, together with light in the vicinity of wavelength 415 nm, it is possible to increase the luminance of the captured image while maintaining the state where superficial blood vessels are being enhanced. Execution of this special observation will be able to obtain information useful for early detection of a lesion such as a malignant tumor.

Examples of the illumination light for the object used in the special observation mode 2 include light in the wavelength range of 528 nm to 584 nm (hereinafter also referred to as "Wide light") and light in the wavelength band of 546 nm to 570 nm (hereinafter also referred to as "Narrow light"). Information regarding the concentration of hemoglobin (oxyhemoglobin and deoxyhemoglobin) in the object is acquired from the captured image of the object under illumination of light in the wavelength range of 528 nm to 584 nm. Oxygen saturation information can be calculated with information regarding the captured image of the object in the wavelength band of 546 nm to 570 nm together with the acquired hemoglobin information, and it is possible to determine the presence or absence of a malignant tumor on the basis of oxygen saturation information and the hemoglobin concentration information. Hereinafter, this processing will be described.

Figure 2:
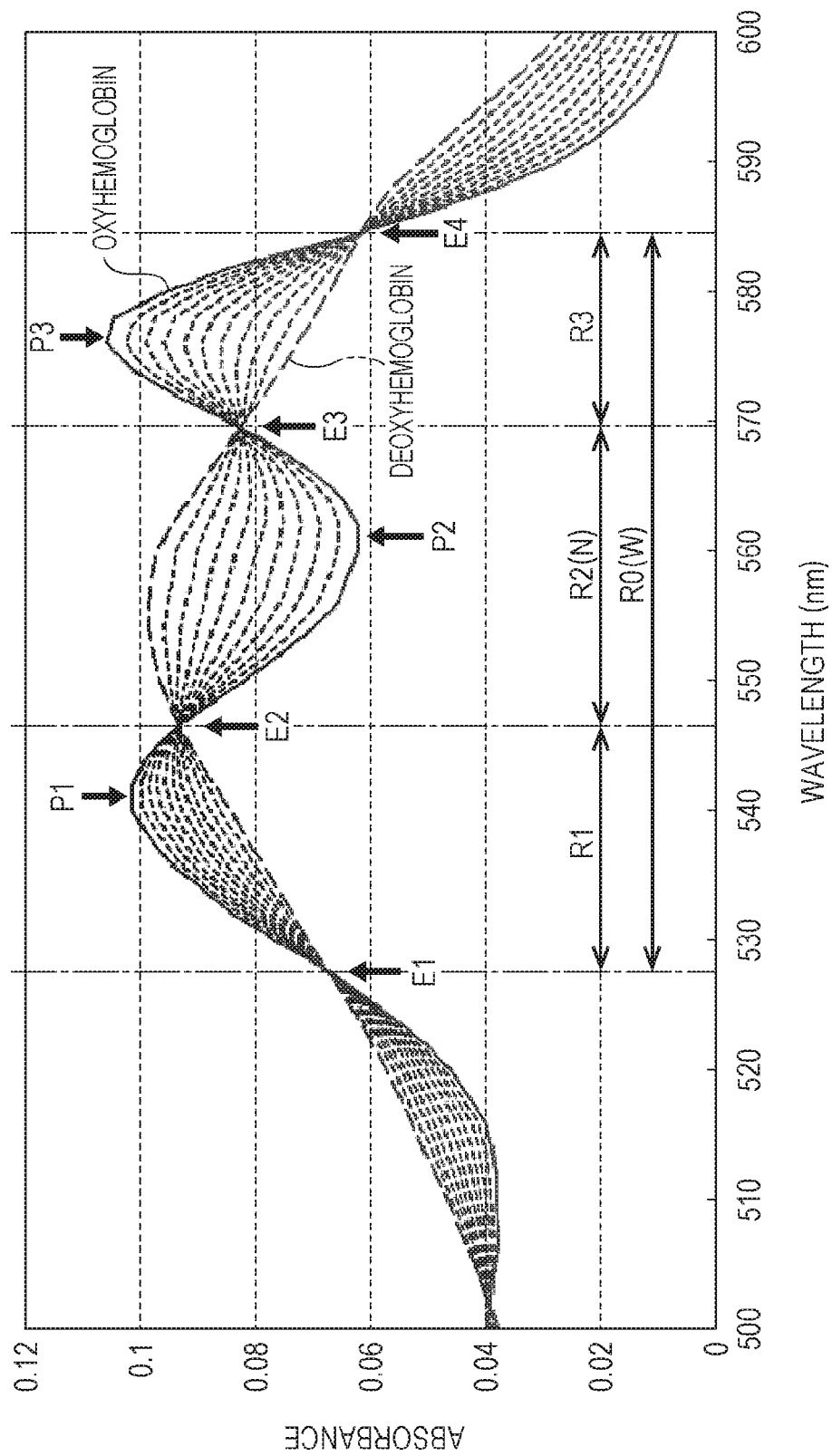
FIG. 2 is a graph illustrating an absorption spectrum of hemoglobin in Q band.

FIG. 2 is a diagram illustrating an absorption spectrum of hemoglobin in Q band. Hemoglobin has a strong absorption band which is referred to as Q band and derived from porphyrin in the vicinity of 550 nm. The absorption spectrum of hemoglobin varies depending on the oxygen saturation. The oxygen saturation is a ratio of oxyhemoglobin HbO to the total hemoglobin. The waveform in solid line in FIG. 2 is an absorption spectrum in a case where the oxygen saturation is 100% (that is, oxyhemoglobin HbO), and the waveform in long broken line is an absorption spectrum in a case where the oxygen saturation is 0% (that is, deoxyhemoglobin Hb), that is, the absorption spectrum of the deoxyhemoglobin Hb. In addition, short broken lines indicate absorption spectrums of hemoglobin at intermediate oxygen saturations of 10, 20, 30, . . . , 90% (mixture of the oxyhemoglobin HbO and the deoxyhemoglobin Hb).

As illustrated in FIG. 2, the oxyhemoglobin HbO and the deoxyhemoglobin Hb have peak wavelengths different from each other in the Q band. Specifically, the oxyhemoglobin HbO has an absorption peak P1 in the vicinity of a wavelength of 542 nm and an absorption peak P3 in the vicinity of a wavelength of 576 nm. In contrast, the deoxyhemoglobin Hb has an absorption peak P2 in the vicinity of 556 nm. FIG. 1 illustrates a two-component absorption spectrum in which the sum of the concentrations of each of components (oxyhemoglobin HbO, deoxyhemoglobin Hb) is constant. This leads to emergence of isosbestic points E1, E2, E3, and E4 at which constant absorption is achieved regardless of the concentration of each of components (that is, oxygen saturation). In the following, the wavelength region between the isosbestic points E1 and E2 is referred to as a wavelength range R1, the wavelength region between the isosbestic points E2 and E3 is referred to as a wavelength range R2, and the wavelength region between the isosbestic points E3 and E4 is referred to as a wavelength range R3. A wavelength region between the isosbestic points E1 and E4 (that is, a combination of the wavelength ranges R1, R2, and R3) is referred to as a wavelength range R0. In the following, the wavelength range R2 is also referred to as a Narrow-band (N-band), and the wavelength range R0 is also referred to as a Wide-band (W-band).

As illustrated in FIG. 2, the absorption of hemoglobin increases or decreases linearly relative to the oxygen saturation in the wavelength ranges between adjacent isosbestic points.

Specifically, levels of absorbance $A_{R1}$ and $A_{R3}$ of hemoglobin in the wavelength ranges R1 and R3 (integrated value at wavelength ranges R1 and R3) increase linearly relative to the concentration of oxyhemoglobin. In addition, absorbance $A_{R2}$ of hemoglobin in the wavelength range R2 increases linearly relative to the concentration of deoxyhemoglobin.

Here, the oxygen saturation is defined by the following Formula 1.

$$Sat = \frac{[HbO]}{[Hb] + [HbO]} \quad \text{[Formula 1]}$$

where,
Sat: Oxygen saturation
[Hb]: Concentration of deoxyhemoglobin
[HbO]: Concentration of oxyhemoglobin
[Hb]+[HbO]: Concentration of Hemoglobin amount (tHb)
In addition, Formula 2 and Formula 3 representing the concentrations of oxyhemoglobin HbO and deoxyhemoglobin are obtained from Formula 1.

$$[Hbo] = Sat \cdot ([Hb] + [HbO]) \quad \text{[Formula 2]}$$

$$[Hb] = (1 - Sat) \cdot ([Hb] + [HbO]) \quad \text{[Formula 3]}$$

Accordingly, the absorbance $A_{R1}$, $A_{R2}$, and $A_{R3}$ of hemoglobin are feature amounts that depend on both the oxygen saturation and the hemoglobin concentration.

Furthermore, according to the research by the present patent applicant, the absorbance $A_{R0}$ of hemoglobin in the wavelength range R0 including the wavelength ranges R1, R2, and R3 (integrated value in the wavelength range R0) is fount out to be determined by the concentration of hemoglobin, independent of the oxygen saturation.

Therefore, the concentration of hemoglobin can be determined from the absorbance $A_{R0}$. Furthermore, the oxygen saturation Sat can be determined on the basis of the absorbance $A_{R1}$, $A_{R2}$, or $A_{R3}$ and the hemoglobin concentration determined from the absorbance $A_{R0}$. As illustrated in FIG. 2, among the wavelength ranges R1, R2, and R3, the amount of change in absorbance due to oxygen saturation (that is, the area of the region surrounded by the waveform in solid line and the waveform in long broken line) is greatest in the wavelength range R2, so as to define the absorbance ARs in the wavelength range R2 as the feature amount having highest sensitivity with respect to the oxygen saturation. For this reason, oxygen saturation is determined using light in the wavelength range R2 (N-band).

Figure 3:
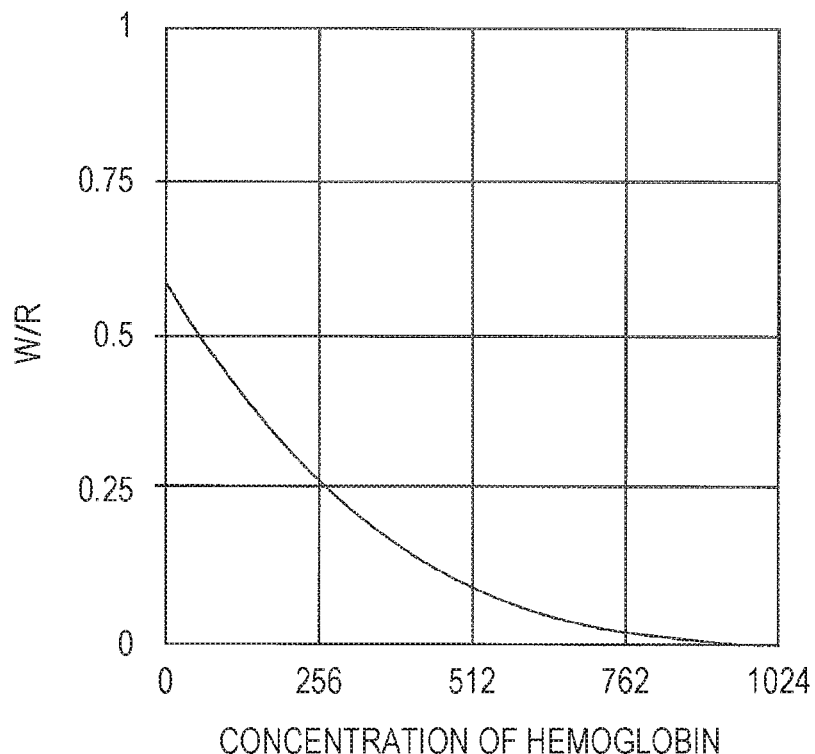
FIG. 3 is a diagram illustrating an example of a relationship between a predetermined ratio and hemoglobin concentration.

FIG. 3 is a diagram illustrating an example of a relationship between a predetermined ratio and hemoglobin concentration. The predetermined ratio is a ratio W/R, which is a ratio obtained by normalizing a value W in the wavelength range of 528 nm to 584 nm of the captured image of the object under illumination of a special ray of light (hereinafter also referred to as "Wide light") in the wavelength range of 528 nm to 584 nm by using a value R being an R image component of the captured image of the object under illumination of white light.

Figure 4:
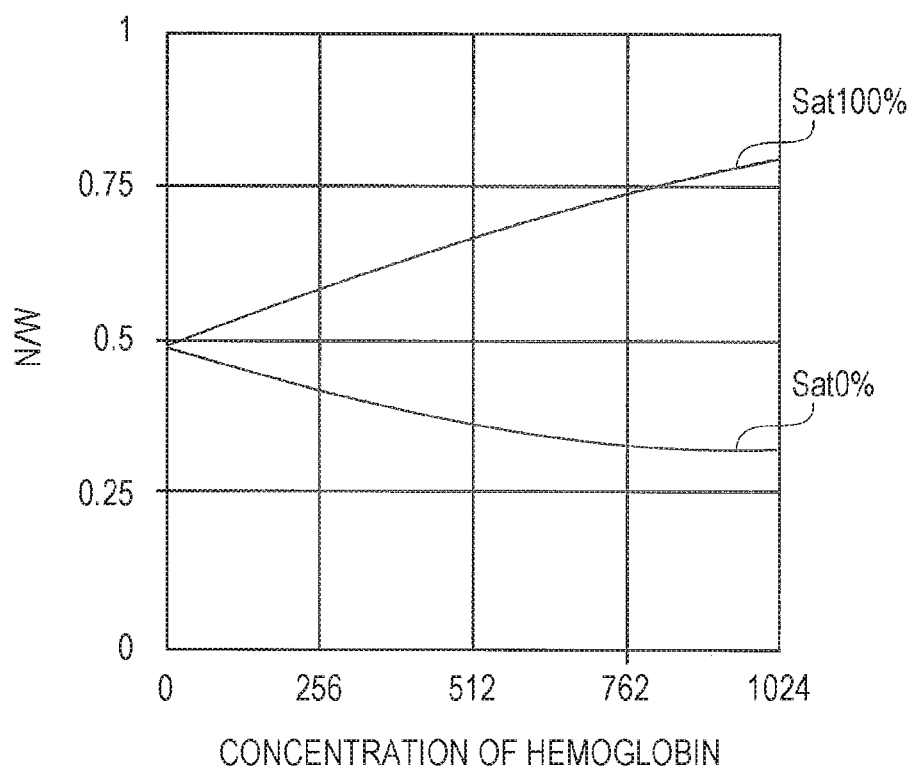
FIG. 4 is a diagram illustrating an example of a relationship between another predetermined ratio and the oxygen saturation level determined by the hemoglobin concentration.

FIG. 4 is a diagram illustrating an example of a relationship between another predetermined ratio and the oxygen saturation level (Sat) determined by the hemoglobin concentration. Another predetermined ratio is a ratio N/W, which is a ratio obtained by dividing a value N in a wavelength range of 546 nm to 570 nm of a captured image of an object under illumination of a special ray of light in a wavelength range of 546 nm to 570 nm (hereinafter also referred to as Narrow light) by the value W in the wavelength range of 528 nm to 584 nm of the captured image of the object under illumination of the special ray of light in the wavelength range of 528 nm to 584 nm. FIG. 4 illustrates an example including curves with oxygen saturation (Sat) of 0% and 100%. Curves of 10%, 20% . . . 90%, or the like exist between the curves of 0% and 100%, at approximately equal intervals. FIG. 4 omits illustrations of curves such as 10%, 20% . . . 90%, or the like.

In this manner, as illustrated in FIG. 3, the concentration of hemoglobin can be calculated from the value of the ratio W/R obtained from the captured image when the special ray of light and white light are used as illumination light. Furthermore, as illustrated in FIG. 4, the oxygen saturation can be calculated from the value of the ratio N/W obtained from the captured image when each of the two special rays of light is used as illumination light and from the calculated hemoglobin concentration.

In this manner, in special observation modes 1 and 2, narrow-band light (special rays of light) having a peak at a specific wavelength, for example, light in the wavelength range in the vicinity of 415 nm, light in the wavelength range in the vicinity of 550 nm, light in the wavelength range in the vicinity of 650 nm, or light in the wavelength range such as N-band or W-band, can be used to perform observation suitable to obtain information such as the running state of blood vessels (blood vessels in each of layers such as the superficial layer, middle layer, deep layer) that are difficult to observe in normal observation mode, or hemoglobin concentration and oxygen saturation.

Figure 6:
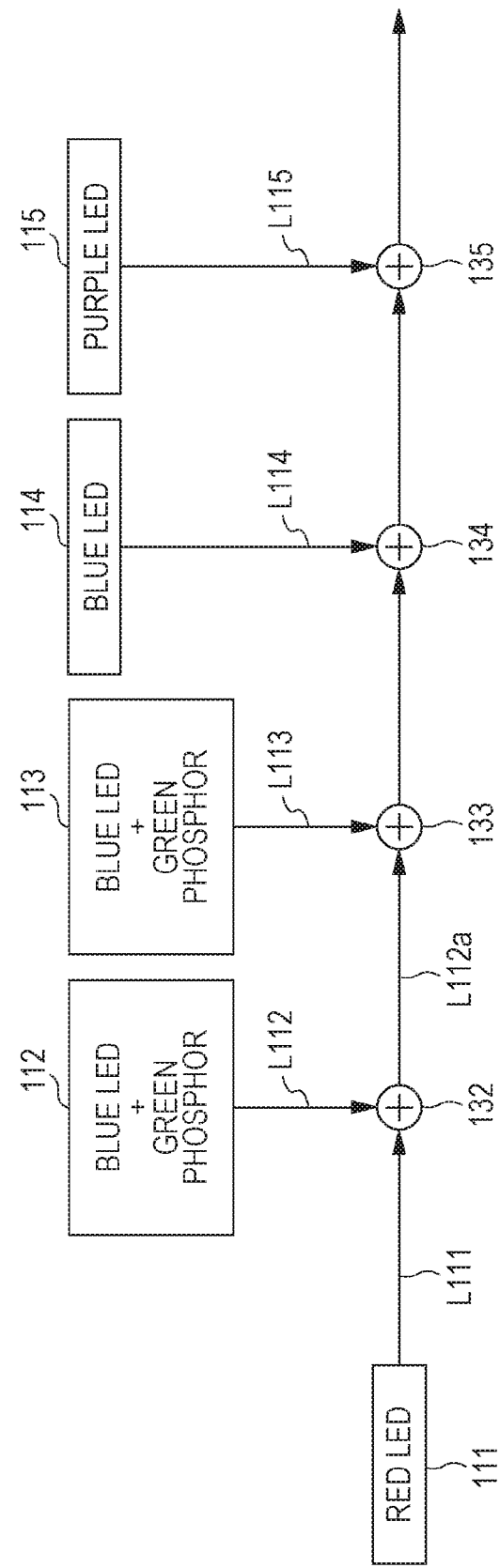
FIG. 6 is a block diagram of the endoscope light source device illustrated in FIG. 5.

The illumination light for the object used in each of observation modes is emitted from the light source device 201 having a configuration illustrated in FIG. 1. FIG. 5 is a diagram illustrating a configuration of the light source device 201 according to an embodiment. FIG. 6 is a block diagram of the light source device 201 illustrated in FIG. 5. The arrangement of the light source unite constituting the light source device 201 illustrated in FIGS. 5 and 6 is an example, and the arrangement of the light source units is not limited to the arrangement of the light source units illustrated in FIGS. 5 and 6.

The light source device 201 includes five light source units 111 to 115, four optical elements 132 to 135, collimating lenses 121 to 125, and a light source drive circuit (control unit) 140.

The light source drive circuit 140 generates a drive current controlled for driving the light source units 111 to 115 and delivers the current to each of the light source units.

Each of the light source units 111 to 115 includes a light emitting diode (LED) that emits light in a wavelength band of a predetermined color.

The collimating lenses 121 to 125 are arranged on an optical path of the emission light on the front surface of each of the light sources 111 to 115, and collimate the emitted light.

The optical elements 132 to 135 have a function of transmitting or reflecting incident light. The optical elements 132 to 135 have configurations in which incident light incident from a first optical path is changed emission light by extracting a light component of a predetermined wavelength band A and removing light components other than the wavelength band A from the incident light, for example, is changed to reflected light, and incident light incident from a second optical path of the optical elements 132 to 135 is changed to emission light by removing the light component of the wavelength band A and extracting light components other than the light component of the wavelength band A from the incident light, for example, is changed to transmitted light. In addition, the first optical path and the second optical path are determined as the optical paths on which the incident light intersects on the optical elements 132 to 135. Accordingly, in a case where the light on the first optical path and the light on the second optical path have passed simultaneously, the reflected light and the transmitted light will be combined into a combined light. That is, the optical elements 132 to 135 are configured to overlap the emission optical path of the passing light that has passed through the first optical path and the emission optical path of the passing light that has passed through the second optical path and to allow emission of the light passing through the overlapping emission optical paths. As the optical elements 132 to 135, for example, dichroic mirrors are used, but are not limited to dichroic mirrors.

Regarding the arrangement of the optical elements 132 to 135, the optical element 132, the optical element 133, the optical element 134, and the optical element 135 are arranged in this order as viewed from the upstream side to the downstream side in the light irradiation direction.

The optical element 132 is provided at a position where the optical path of light incident from the light source unit 111 and the optical path of light incident from the light source unit 112 intersect with each other. The optical element 133 is provided at a position where the optical path of the light incident from the optical element 132 and the optical path of the light incident from the light source unit 113 intersect with each other. The optical element 134 is provided at a position where the optical path of the light incident from the optical element 133 and the optical path of the light incident from the light source unit 114 intersect with each other. The optical element 135 is provided at a position where the optical path of the light incident from the optical element 134 and the optical path of the light incident from the light source unit 115 intersect with each other.

Here, beams of the light of at least a part of the wavelength band of the light emitted from the light source unit 111 and the light of at least a part of the wavelength band of the light emitted from the light source unit 112 turn to be combined light in the optical element 132 due to overlapping of their optical paths, and then, the combined light is emitted from the optical element 132. Furthermore, beams of the light of at least a part of the wavelength band of the light emitted from the optical element 132 and the light of at least a part of the wavelength band of the light emitted from the light source unit 113 turn to be combined light in the optical element 133 due to overlapping of their optical paths, and then, the combined light is emitted from the optical element 133. Furthermore, beams of the light of at least a part of the wavelength band of the light emitted from the optical element 133 and the light of at least a part of the wavelength band of the light emitted from the light source unit 114 turn to be combined light in the optical element 134 due to overlapping of their optical paths, and then, the combined light is emitted from the optical element 134.

Furthermore, beams of the light of at least a part of the wavelength band of the light emitted from the optical element 134 and the light of at least a part of the wavelength band of the light emitted from the light source unit 115 turn to be combined light in the optical element 135 due to overlapping of their optical paths, and then, the combined light is emitted from the optical element 135.

Filter characteristics regarding removal and extraction of light are adjusted so that the above-described wavelength band A in the optical element 132 is set to a wavelength band in the range of 600 nm or less, specifically, a wavelength band of 528 nm to 584 nm, for example. That is, the transmitted light of the optical element 132 is to be light from which the light component of the wavelength band A, for example, 528 nm to 584 nm is removed, while the reflected light of the optical element 132 is to be light from which the light component of the wavelength band A, for example, 528 nm to 584 nm is extracted.

Filter characteristics regarding removal and extraction of light are adjusted so that the above-described wavelength band A in the optical element 133 is set to a wavelength band in the range of 600 nm or less, and a narrower wavelength band A in the optical element 132, for example, a wavelength band of 546 nm to 570 nm. That is, the transmitted light of the optical element 133 is to be light from which the light component of the wavelength band A, for example, 546 nm to 570 nm is removed, while the reflected light of the optical element 133 is to be light from which the light component of the wavelength band A, for example, 546 nm to 570 nm is extracted.

The filter characteristics regarding removal and extraction of light are adjusted so that the above-described wavelength band A in the optical element 134 is set to a wavelength band of 515 nm or less, for example. That is, the transmitted light of the optical element 134 is to be light from which the light component of the wavelength band A, for example, 515 nm or less, is removed, while the reflected light of the optical element 134 is to be light from which the light component of the wavelength band A, for example, 515 nm or less, is extracted.

The above-described wavelength band A in the optical element 135 is adjusted in characteristics so as to be a wavelength band of 430 nm or less, for example. That is, the transmitted light of the optical element 135 is to be light from which the light component of the wavelength band A, for example, 430 nm or less, is removed, while the reflected light of the optical element 135 is to be light from which the light component of the wavelength band A, for example, 430 nm or lees, is extracted.

Hereinafter, in order to distinguish individual wavelength bands A of the optical elements 132 to 135, the bands will be referred to as wavelength bands A132 to A135.

The light source unit 111 includes a red LED that emits light in a red wavelength band (for example, wavelength: 620 nm to 680 nm).

The light source unit 112 includes a blue LED 112a that emits light in a blue wavelength band (for example, wavelength: 430 nm to 470 nm), and a green phosphor 112b. The green phosphor 112b is excited by the blue LED light emitted from a blue LED 113a, and emits fluorescence in the green wavelength band (for example, wavelength: 460 nm to 600 nm).

Similarly to the light source unit 112, the light source unit 113 includes the blue LED 113a that emits light in the blue wavelength band (for example, wavelength: 430 nm to 470 nm), and a green phosphor 113b. The green phosphor 113b is excited by the blue LED light emitted from a blue LED 113a, and emits fluorescence in the green wavelength band (for example, wavelength: 460 nm to 600 nm).

In the present embodiment, the light source unit 113 includes the green phosphor 113b, although a yellow phosphor may be used instead of the green phosphor 113b. The yellow phosphor is excited by blue LED light emitted from the blue LED, and emits fluorescence in a yellow wavelength band (for example, wavelength: 435 nm to 480 nm).

The light source unit 114 includes a blue LED that emits light in a blue wavelength band (for example, wavelength: 430 nm to 470 nm). The light source unit 115 includes a purple LED that emits light in a purple wavelength band (for example, wavelength: 395 nm to 435 nm). The purple wavelength band includes at least a wavelength of 415 nm.

Figure 7:
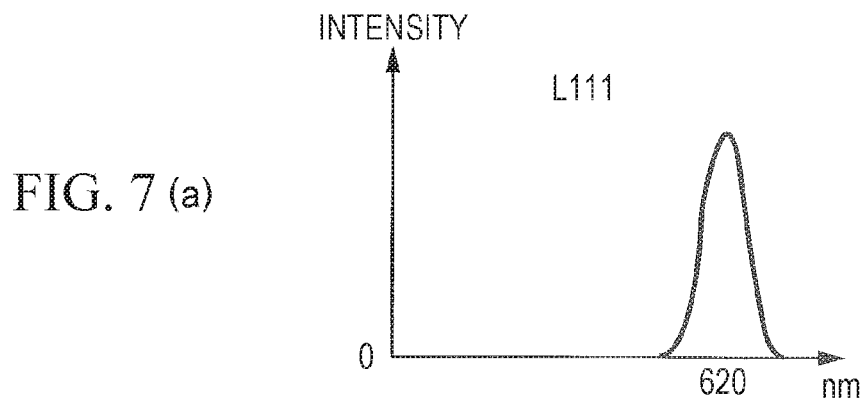
FIGS. 7(a) to 7(d) are diagrams illustrating an example of spectral intensity distribution of light emitted from an endoscope light source device according to an embodiment.
Figure 7:
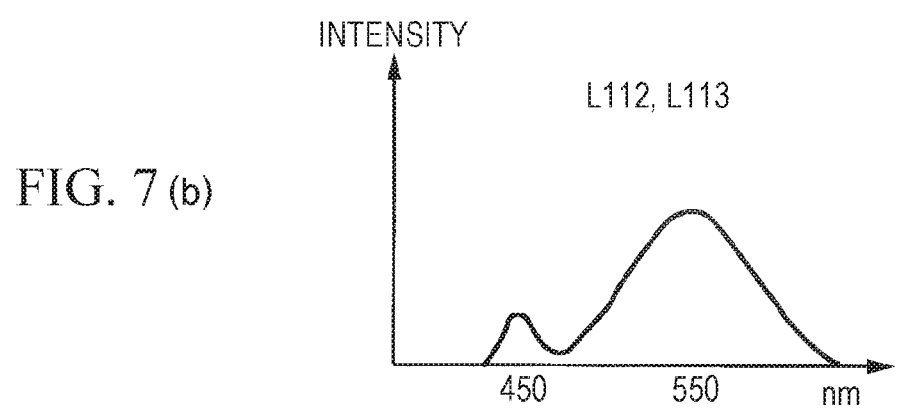
Figure 7:
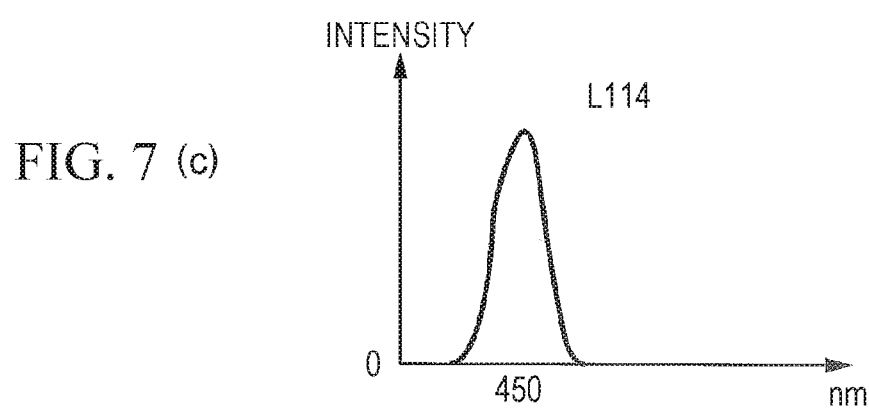
Figure 7:
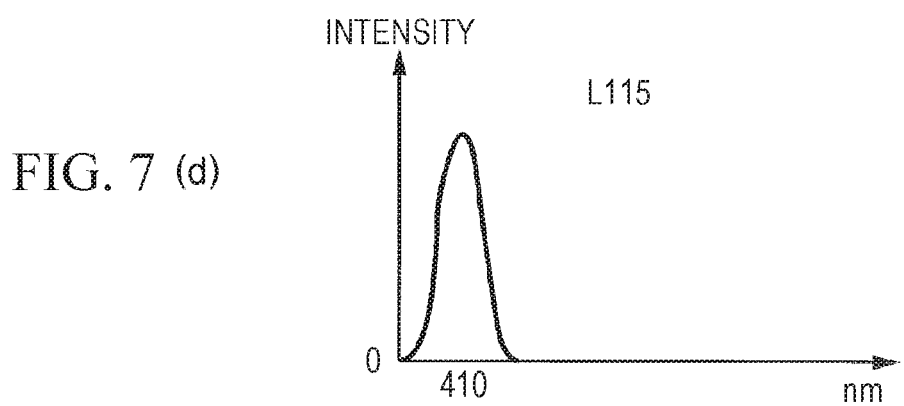

FIGS. 7(a) to 7(d) are diagrams illustrating examples of spectral intensity distribution of the light emitted from the light source device 210. FIG. 7(a) illustrates an example of spectral distribution of light intensity of light L111 emitted from the light source unit 111. FIG. 7(b) illustrates an example of spectral distribution of the light intensity of light L112 and L113 emitted from the light source units 112 and 113, respectively. FIG. 7(c) illustrates an example of spectral distribution of the light intensity of light L114 emitted from the light source unit 114. FIG. 7(d) illustrates an example of spectral distribution of the light intensity of light L115 emitted from the light source unit 115.

Here, the light source unit 113 is configured to emit the light L113 including at least a light component in the wavelength band A133 of the optical element 133, for example, 546 nm to 570 nm, and configured to allow the light L113 to be incident onto the optical element 133 so as to allow the light L113 to be incident from the first optical path (optical path as reflected light) of the optical element 133 to be reflected light of the wavelength band A133.

In contrast, the light source unit 112 is configured to emit the light L112 including at least a light component in the wavelength band A132 of the optical element 132, for example, 528 nm to 584 nm, and configured to allow light L112a (refer to FIG. 9(a)) of the wavelength band A133 that at least includes a light component of the wavelength band A133 obtained from the light L112 by reflection on the optical element 132 to be incident from the optical element 132 to the optical element 133 through the second optical path (optical path as transmitted light) of the optical element 133.

FIG. 8(a) is an example of a characteristic of transmittance in the transmitted light and a characteristic of reflectance in the reflected light of the optical element 132. FIG. 8(b) is an example of a characteristic of transmittance in the transmitted light and a characteristic of reflectance in the reflected light of the optical element 133. FIGS. 9(a) to 9(c) are diagrams illustrating an example of spectral intensity distribution of light that has passed through the optical element 133.

As illustrated in FIG. 8(b), filter characteristics regarding removal and extraction of light are adjusted so that the above-described wavelength band A133 in the optical element 133 is set to a narrower wavelength band (for example, wavelength band of 546 nm to 570 nm) among wavelength band A132 (for example, wavelength band of 528 nm to 584 nm) in the optical element 132 illustrated in FIG. 8(a). Accordingly, the transmitted light, namely, the light L112a (refer to FIG. 9(a)) incident from the optical element 132 onto the optical element 133 and then transmitted through and emitted from the optical element 133 is to be light obtained by removing the light component of the wavelength band A133 in the optical element 133 from the light L112a (refer to FIG. 9(b)). In the optical element 133, however, the transmitted light from the optical element 133 and the reflected light (refer to FIG. 9(c)) in the wavelength band A133 (for example, the wavelength band of 546 nm to 570 nm) set in the optical element 133, out of the light L113 emitted from the light source unit 113, are combined. Accordingly, the combined light is emitted from the optical element 133 as light from which the light component in the wavelength band A133 (for example, the wavelength band of 546 nm to 570 nm) in the optical element 133 is not removed.

Therefore, the light source drive circuit 140 controls the driving so that, when the light source unit 112 emits the light L112, the light source unit 113 emits the light L113 at the same time, making it possible to emit, from the optical element 133, combined light obtained by adding the light component (reflected light in the optical element 133) of the wavelength band A132 in the optical element 132 in the light L113 to the light (transmitted light in the optical element 133) obtained by removing the light component of the wavelength band A132 in the optical element 132 from the light L112a in the wavelength band A in the optical element 133. In contrast, the light source drive circuit 140 controls the driving so that the light L112 is not to be emitted from the light source unit 112 when the light source unit 113 emits the light L113, making it possible to emit, from the optical element 133, reflected light including a light component in the wavelength band A133 in the optical element 133.

That is, the light source drive circuit 140 controls on/off of the emission of the light L112 and emission of the light L113, making it possible to selectively emit special rays of light 1 and 2 (for example, Narrow light and Wide light). Specifically, turning on the emission of the light L112 and the emission of the light L113 to combine the light L112a and the light L113 obtained by the optical element 132 enables generation of the special ray of light 2, for example, the above-described Wide light, including a light component of the wavelength band A (for example, the wavelength band of 528 nm to 584 nm) in the optical element 132. Alternatively, turning off the emission of the light L112 while turning on the emission of the light L113 to allow the emission of the reflected light from the optical element 133 enables generation of the special ray of light 1, for example, the above-described Narrow light, including a light component of the narrow wavelength band (for example, the wavelength band of 546 nm to 570 nm) included in the wavelength band of the special ray of light 2.

In this manner, it is possible to easily perform switching between the special rays of light 1 and 2 as the illumination light of the object, without using a rotating optical filter as in the conventional light source device.

Figure 10:
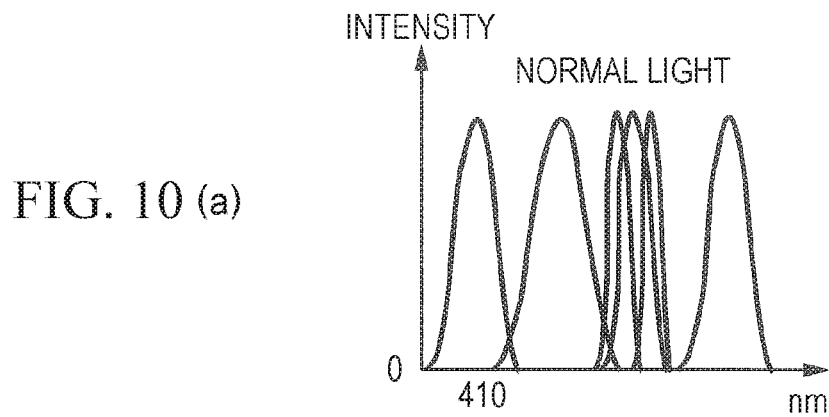
FIG. 10(a) is a diagram illustrating an example of spectral intensity distribution of white light (normal light) emitted from an endoscope light source device of an embodiment.
FIGS. 10(b) to 10(d) are diagrams illustrating an example of spectral intensity distribution of special rays of light emitted from an endoscope light source device according to an embodiment.
Figure 10:
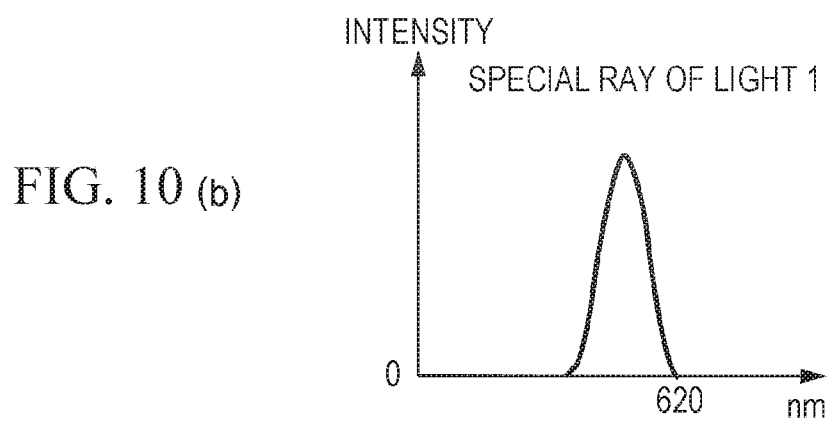
Figure 10:
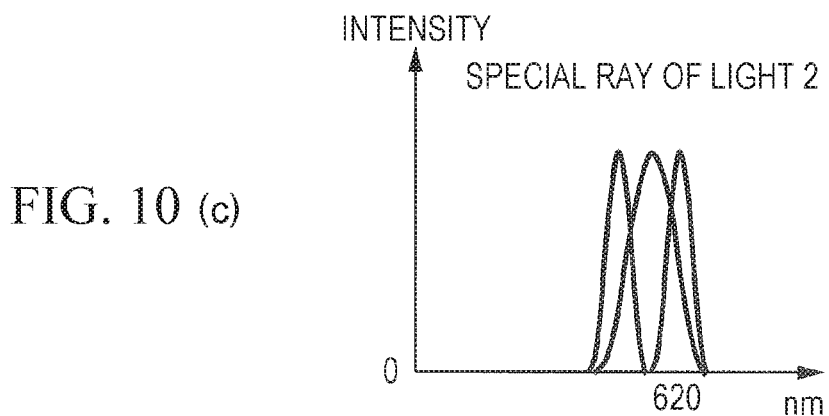
Figure 10:
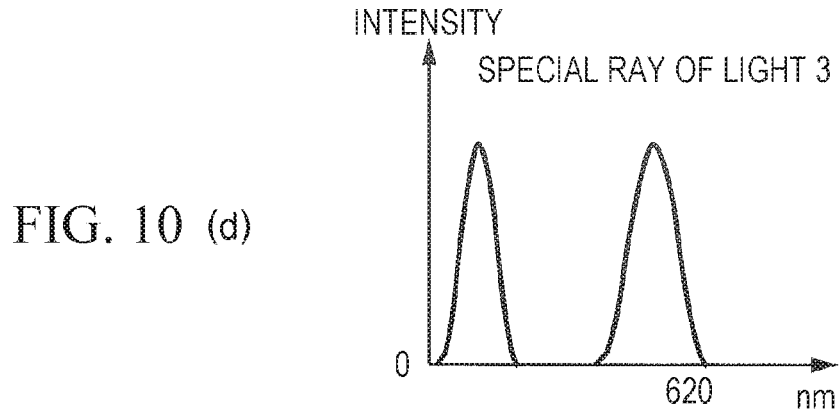

FIGS. 10(*a*) to 10(*d*) are diagrams illustrating examples of light intensity distribution of normal light (white light) and special rays of light 1 to 3 emitted from the light source device 201 as illumination light. In FIGS. 10(*a*) to 10(*d*), the peak values in the intensity distribution of a plurality of light beams are illustrated to be the same. However, the maximum intensity peak values may be the same or different from each other.

The normal light illustrated in FIG. 10(*a*) is obtained by emitting each of light beams from the light source units 111 to 115. This normal light is used as illumination light used in the normal observation mode. Normal light is used as illumination light for illumination between the usage of special rays of light as illumination light in the special observation modes 1 and 2.

The special ray of light 1 illustrated in FIG. 10(*b*) is obtained by emitting light from the light source unit 113 alone.

The special ray of light 2 illustrated in FIG. 10(*c*) is obtained by emitting light from both the light source units 112 and 113. The special rays of light 1 and 2 are used as Narrow light and Wide light being illumination light in the special observation mode 2. According to an embodiment, the special ray of light 2 is also preferably used as illumination light for enhancing blood vessels in the special observation mode 1.

A special ray of light 3 illustrated in FIG. 10(*d*) is obtained by emitting light from both the light source units 113 and 115. The special ray of light 3 is used as illumination light for enhancing blood vessels in the special observation mode 1.

Figure 9:
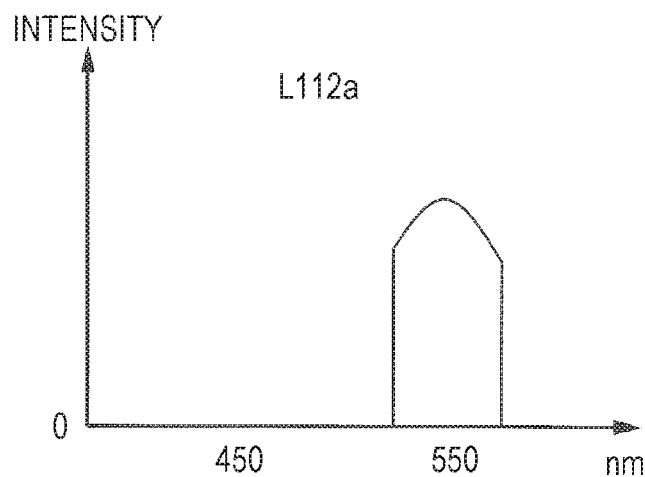
FIGS. 9(a) to 9(c) are diagrams illustrating an example of spectral intensity distribution of light that has passed through an optical element.
Figure 9:
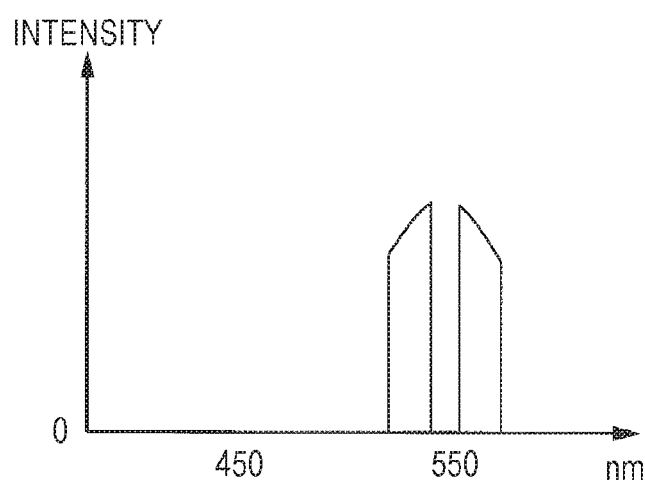
Figure 9:
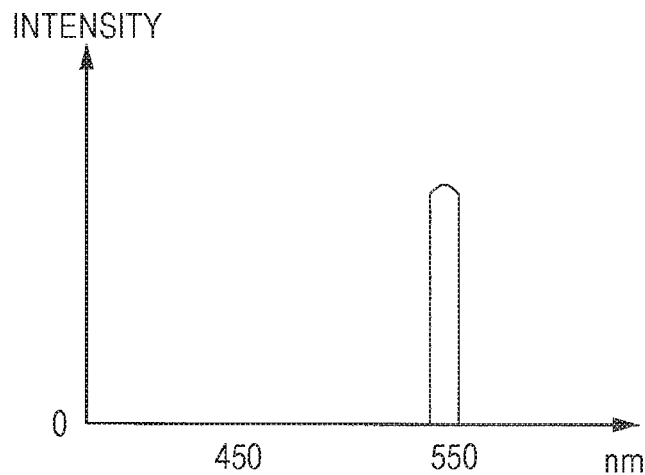

The light intensity distribution patterns in FIGS. 9(*b*) and 9(*c*) are schematically illustrated for easy understanding such that the light intensity distribution has a shape rising sharply. In practice, however, the light intensity distribution in FIG. 9(*c*) changes gently as illustrated in FIG. 10(*b*) in accordance with filter characteristics of the optical element. For this reason, as illustrated in FIG. 10(*c*), three peak values are likely to appear in the light intensity distribution. For this reason, according to an embodiment, it is preferable that the light source drive circuit (control unit) 140 controls the blue LED of the light source unit 113 so as not to generate light intensity distribution as illustrated in FIG. 10(*c*) having three peak values, that is, so as to form a single peak value in the intensity distribution in the combined light with a gentle intensity distribution. In order to achieve this, the light source drive circuit (control unit) 140 preferably controls the blue LED such that the light intensity of the light L113 when generating the special ray of light 1 differs from the light intensity of the light L113 when generating the special ray of light 2.

As described above, the optical element 132 is configured to generate emission light (light L112*a*) to be emitted to the optical element 133 so as to become transmitted light at the optical element 133 in response to incidence of the light L112 from the light source unit 112. Therefore, with a configuration of overlapping the emission optical path of the transmitted light in the optical element 133 and the emission optical path of the reflected light in the optical element 133, it is possible, with a simple configuration, to easily generate combined light having a wavelength band such as the special ray of light 2 that combines the transmitted light and the reflected light.

Note that, according to an embodiment, the wavelength band of the light L112 and the wavelength band of the light L113 are preferably the same. With this configuration, it is possible to implement generation of the special ray of light 1 and the generation of the special ray of light 2 in a wide wavelength band including the wavelength band of the special ray of light 1 by simply switching on/off of the emission of the light L112 of the light source unit 112 while turning on the emission of the light L113 of the light source unit 113, leading to achievement of generation of the special rays of light 1 and 2 with a simple configuration.

According to an embodiment, as illustrated in FIG. 6, the optical element 132 overlaps the emission optical path (emission optical path of transmitted light) of the light L111 and the emission optical path (emission optical path of reflected light) of the light L112 in response to the incidence of the light L111 and the light L112, and emits light that passes through the overlapped emission optical path to the optical element 133, making it possible to easily combine normal light (white light).

Furthermore, according to an embodiment, the optical element 134 or the optical element 135 receives incidence of the emission light from the light source unit 114 or the light source unit 115 and the emission light from the optical element 133, and the emission optical paths of these rays of light are overlapped, then, the combined light passing through the overlapped emission optical path is emitted as normal light (white light). Accordingly, it is possible to easily combine normal light (white light).

In the embodiment described above, the light source unit 111 including the red LED that emits light in the red wavelength band (for example, wavelength: 630 nm to 670 nm) is provided upstream in the light emission direction with respect to the optical element 132. Alternatively, according to an embodiment, the light source unit 111 may be provided downstream in the light emission direction with respect to the optical element 132. In this case, the light source unit 114 including a blue LED that emits light in a blue wavelength band (for example, wavelength: 430 nm to 470 nm), and the light source unit 115 including the purple LED that emits light in a purple wavelength band (for example, wavelength: 395 nm to 435 nm) are provided upstream in the light emission direction with respect to the optical element 132. In this case, filter characteristics regarding removal and extraction of light components of the optical elements 132 to 135 are appropriately adjusted in accordance with the wavelength. For example, the filter characteristics of the optical elements 132 to 134 are adjusted so that the transmitted light is light of a light component in the wavelength band of each of optical elements, and that the reflected light is light from which the light component of the wavelength band of each of optical elements is removed.

Accordingly, the optical element 132 is configured to receive the incidence of light in the blue wavelength band or the light in the purple wavelength band and the light L112, and overlap the light emission paths of these rays of light, and allow the combined light passing through the overlapping emission optical paths to be emitted to the downstream optical element. Moreover, it is configured such that, in response to the incidence of the light in the red wavelength band and the emission light from the upstream optical element, the emission optical paths of these rays of light are overlapped, and then, the combined light in the overlapping emission optical paths is emitted as normal light (white light). This makes it possible to easily combine the normal light (white light).

According to an embodiment, the light source drive circuit (control unit) 140 is configured to control the driving of the light source unit 112, the light source unit 113, the light source unit 111, and the light source units 114 and 115 so as to repeatedly emit the special ray of light 1, the special ray of light 2, and the normal light (white light), as emission light. Therefore, with the switching of on/off of the emission of the emission light of the light source unit, it is possible to easily switch the normal light, the special rays of light 1 to 3 without providing a rotation filter as in a conventional example.

The light source unit 113 or the light source unit 112 respectively includes the blue LED 113a (first solid state light emitting element) or a blue LED 112a (second solid-state light emitting element) that emits excitation light (first excitation light or second excitation light), and respectively includes the green phosphor 113b (first phosphor) or the green phosphor 112b (first phosphor) that emits fluorescence (first fluorescence or second fluorescence) by the excitation light. The light L113 from the light source unit 113 includes the above-described excitation light and fluorescence. In particular, the wavelength bands A132 and A133 respectively set in the optical element 132 and the optical element 133 are preferably included in the wavelength band of the fluorescence emitted by the green phosphor 113b or the green phosphor 112b. In this manner, the wavelength band of the light L113 can be varied by changing the type of phosphor, making it possible to easily change the wavelength band of the light L113.

The above-described special ray of lights 1 and 2 are examples using the light in the wavelength band of 528 nm to 584 nm and the light of 546 nm to 570 nm illustrated in FIG. 2. Alternatively, however, the special ray of lights 1 and 2 may be the light in a narrow wavelength band of 400 nm to 422 nm or the light in a wide wavelength band of 400 nm to 452 nm. With this configuration, it is possible to obtain information regarding the oxygen saturation and the hemoglobin concentration. In this case, it is preferable that the light source unit 112 emits light in a wavelength band including at least a wide wavelength band of 400 nm to 452 nm, and the optical element 132 generates reflected light in the wavelength band of 400 nm to 452 nm, and that the reflected light be incident so that the reflected light will be the transmitted light in the optical element 133. It is preferable that the light source unit 113 emits light in a wavelength band including at least a narrow wavelength band of 400 nm to 422 nm, and the optical element 133 generates reflected light in a wavelength band of 400 nm to 422 nm. This enables the combined light in the optical element 133 to generate the special ray of light 2 in the wavelength band of 400 nm to 452 nm. In contrast, in a case of generating the special ray of light 1, the light emission of the light source unit 112 is turned off, and the light of the light source unit 113 is emitted, thereby generating the special ray of light 1. According to an embodiment, the above-described narrow wavelength band is preferably 422 nm to 452 nm instead of 400 nm to 422 nm.

As for the blue phosphors 112b and 113b used respectively in the light source units 112 and 113, oxide phosphors or nitride-based phosphors are preferably used, for example.

Oxide phosphors include green phosphors with Ce activated by calcium scandium silicon oxide ($Ca_3Sc_2Si_3O_{12}$) as base crystal, or green phosphors with Ce activated by calcium scandium oxide ($CaSc_2O_4$) as base crystal.

Nitride-based phosphors include sialon phosphors in which trace amounts of metal ions responsible for light emission of rare earth elements or the like are added to the base ceramic crystal, α-sialon phosphors that are solid solutions of α-type silicon nitride ($Si_3N_4$) crystals, and calcium nitride aluminum silicon ($CaAlSiN_3$) phosphors.

As described above, in a case where a yellow phosphor is used instead of the green phosphor, the oxide phosphor used as the yellow phosphor includes a yellow phosphor having yttrium aluminum oxide ($Y_3Al_5O_{12}$) as a base crystal.

Nitride-based phosphors used as yellow phosphors include sialon phosphors in which trace amounts of metal ions responsible for light emission of rare earth elements or the like are added to the base ceramic crystal, α-sialon phosphors that are solid solutions of α-type silicon nitride ($Si_3N_4$) crystals, and calcium nitride aluminum silicon ($CaAlSiN_3$) phosphors.

The above embodiment has described an example of the light source units 112 and 113 that generate fluorescence in the green wavelength band from the excitation light in the blue wavelength band and emit the fluorescence together with the excitation light. However, according to an embodiment, it is also preferable to use, for the light source units 112 and 113, a fluorescent LED that emits, together with the excitation light, fluorescence in the green wavelength band emitted by the phosphor by excitation light in the green wavelength band, for example, fluorescence having a maximum intensity peak wavelength in 570 nm to 580 nm in the wide wavelength band of 500 to 700 nm.

Figure 11:
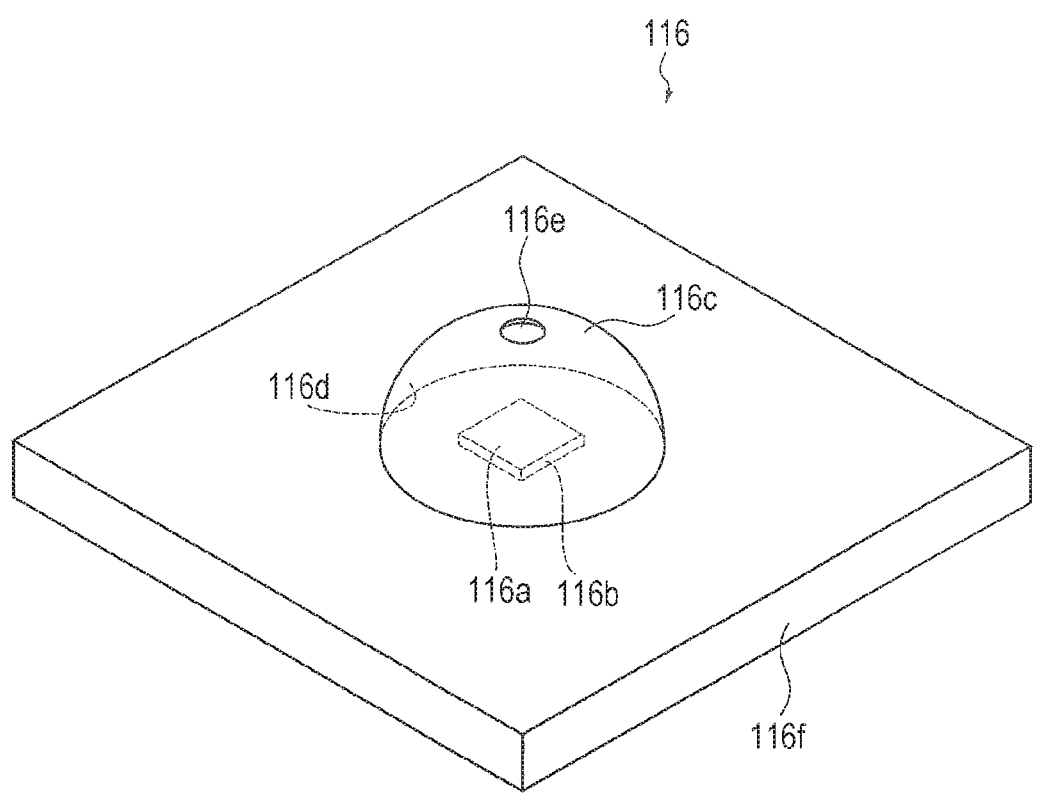
FIG. 11 is a view illustrating a configuration of a light source unit according to another embodiment.

FIG. 11 is a view illustrating another embodiment of the light source units 111 to 115 including LEDs. In any one of the light source units 111 to 115, in order to increase the intensity of the emitted light, according to an embodiment, it is preferable to dispose a cover member including a reflector so as to cover the light emission surface of the light source unit, as illustrated in FIG. 11, Specifically, there is provided a cover member 116c that covers an LED 116b in a state of being spaced from a light emission surface 116a in a light source unit 116 (the light source units 111 to 115 will be represented as the light source unit 116). The cover member 116c includes a reflection surface 116d that reflects light emitted from the light emission surface 116a, and an opening 116e through which light is emitted from a space surrounded by the cover member 116c. The LED 116b is provided on a substrate 116f. The light emitted from the light emission surface 116a is diffused and emitted as diffused light, but the light emitted in the direction other than the opening 116e is reflected toward the substrate 116f or the LED 116b by the reflection surface 116d of the cover member 116c. The light reflected by the reflection surface 116d is reflected again toward the opening 116e or the cover member 116c by the substrate 116f or the LED 116b. In this manner, the light is repeatedly reflected in the space inside the cover member 116c until the light travels in the direction of the opening 116e. Finally, the light passes through the opening 116e and is emitted from the light source unit 116. This configuration increases the light intensity of the light emitted from the opening 116e. It is preferable that the LED 116b has a configuration in which a fluorescent LED emits, from the light emission surface 116a, the fluorescence that is emitted from the phosphor using the generated excitation light, from the viewpoint that the light intensity of the fluorescence can be increased. In this case, the reflected excitation light is incident on the phosphor many times in the process of repeated reflection of the excitation light in the space inside the cover member 116c, leading to an increase in the light intensity of the fluorescence emitted by the phosphor. Therefore, it is preferable that the light source units 112 and 113 include reflection surfaces (first reflection surface, second reflection surface) respectively to cover a part of the space around the light emission surface of the light source so as to cause a part of the excitation light (first excitation light and second excitation light) that has passed without exciting the phosphors (first phosphor and second phosphor) to be reflected and emitted to the phosphor to increase the intensity of the fluorescence emitted by the phosphor.

Figure 12:
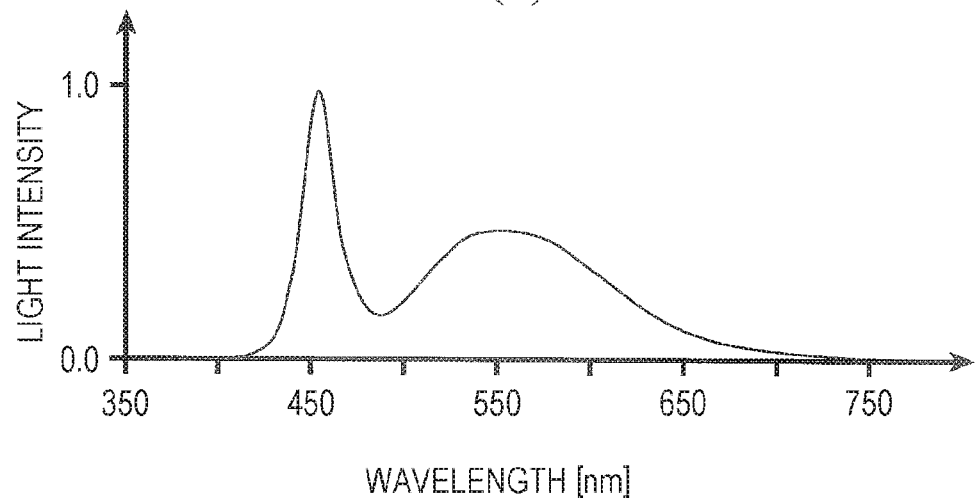
FIG. 12(a) is a diagram illustrating an example of a light intensity distribution of a light source unit without a cover member.
FIG. 12(b) is a diagram illustrating an example of a light intensity distribution of the light source unit illustrated in FIG. 11.
Figure 12:
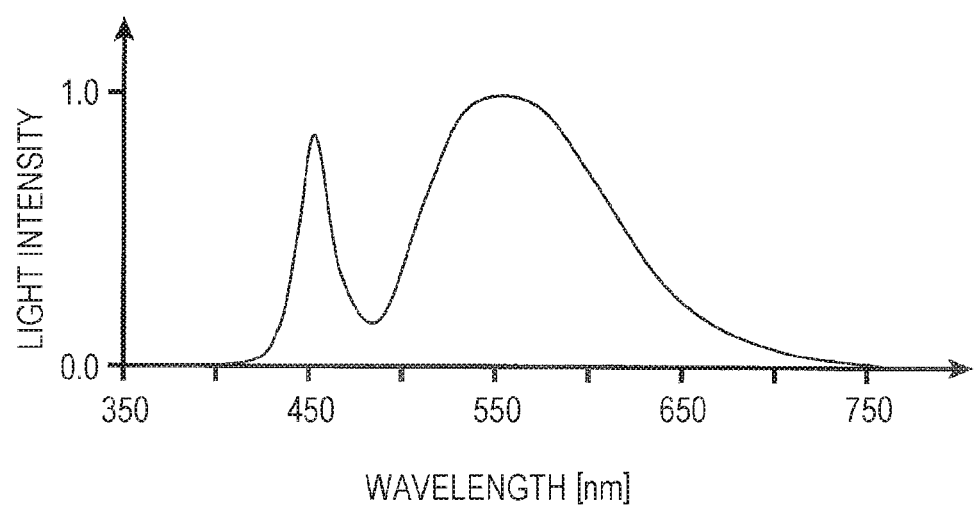

FIG. 12(a) is a diagram illustrating an example of a light intensity distribution of light emitted from the light source unit without the cover member 116c. FIG. 12(b) is a diagram illustrating an example of a light intensity of light emitted from the light source unit 116 illustrated in FIG. 11. Specifically, FIGS. 12(a) and 12(b) respectively illustrate examples of light intensity distribution of excitation light (light having steep light intensity distribution having a peak wavelength of light intensity at 450 nm) and light intensity distribution of fluorescence (light having gentle light intensity distribution having a peak wavelength of light intensity near 550 nm) in a case where the cover member 116c is not provided and a case where the cover member 116c is provided. In this manner, providing the cover member 116c makes it possible to increase the light intensity of the fluorescence.

In this manner, the cover member 116c is capable of increasing the light intensity of the fluorescence. For example, special ray of light used for illumination of biological tissue is light with a narrow wavelength band, and thus the amount of light as illumination light would be insufficient. This tends to cause generation of a dark captured image obtained by special ray of light. However, the use of the cover member 116 makes it possible to increase the light intensity of the special ray of light without increasing the drive current for light emission given to the light source unit 116. Furthermore, in a case where the special ray of light is used as one light component of normal light (white light), the light intensity can be increased so as to cope with the large light intensity of other light components. In this manner, the effect of using the cover member 116c is great.

Figure 13:
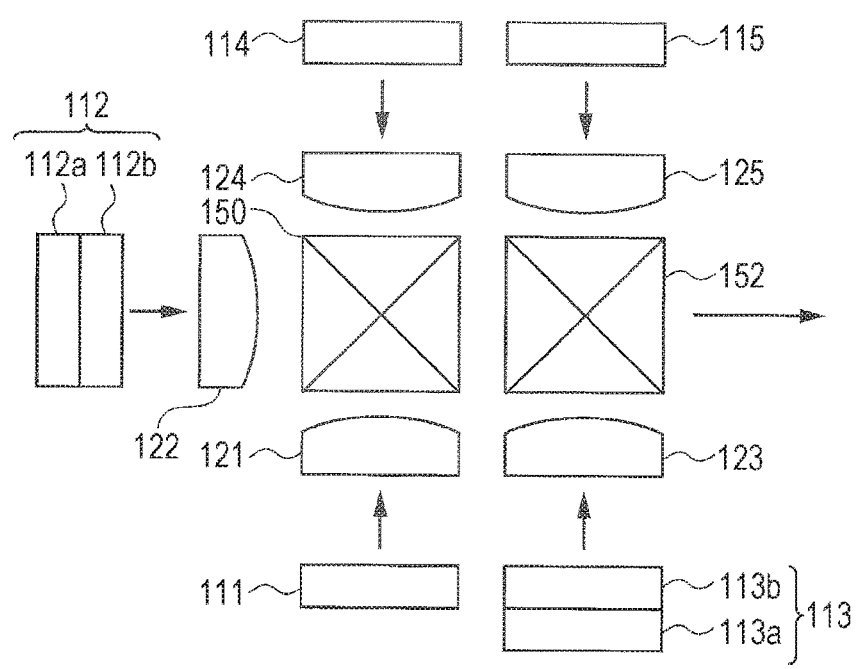
FIGS. 13(a) and 13(b) are diagrams illustrating an example of a configuration of an endoscope light source device according to an embodiment.
Figure 13:
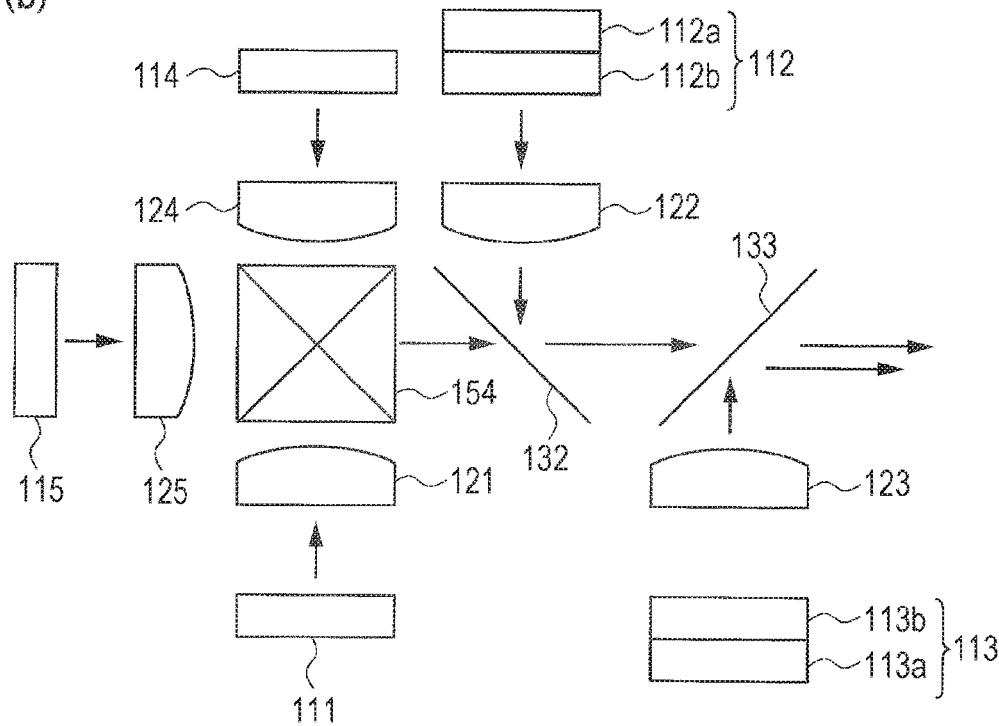

FIGS. 13(a) and 13(b) are diagrams illustrating an example of a configuration of the light source device according to an embodiment. Here, the configuration is more compact than the configuration illustrated in FIG. 5. The light source units 111 to 115 are the same as the light source units 111 to 115 illustrated in FIG. 5.

In the configuration illustrated in FIG. 13(a), a cross prism or a dichroic prism is used as the two optical elements 150 and 152. With this configuration, the light source units 111 to 115 can be compactly arranged around the optical element 150.

In the configuration illustrated in FIG. 13(b), a cross prism or a dichroic prism is used as one optical element 154. Optical elements 132 and 133 that are dichroic mirrors are used as the other optical elements. With such a configuration, light from the light source units 112 and 113 can be efficiently used and emitted as emission light from the light source device 201 as compared with the configuration illustrated in FIG. 13(a). According to an embodiment, as illustrated in FIGS. 13(a) and 13(b), it is preferable that the compact light source device having a configuration that uses an optical element of the cross prism or the dichroic prism and that arranges the light source unit at least at two positions on both sides of the optical element, is provided at the distal end portion of the electronic scope 100. In the arrangement of the light source unit illustrated in FIGS. 13(a) and 13(b), the optical element 150 or the optical element 132 is configured so as to receive incidence of light L112 from the light source unit 112 and generate emission light to be emitted toward the optical element 152 or the optical element 133 so as to allow the light to be transmitted light at the optical element 152 or the optical element 133. Therefore, overlapping the emission optical path of the transmitted light in the optical element 152 or the optical element 133 and the emission optical path of the reflected light in the optical element 152 or the optical element 133 makes it possible to easily generate the combined light in a wavelength band such as the special ray of light 2, obtained by combining the transmitted light and the reflected light, with a simple configuration.

While in the electronic endoscope system 1 illustrated in FIG. 1, the light source device 201 is provided in the processor 200, the light source device 201 may be configured as a device separate from the processor 200 and the electronic scope 100.

According to an embodiment, the electronic scope 100 may incorporate the light source units 111 to 115 as a light source device. At this time, according to an embodiment, it is preferable that the light source units 111 to 115 be incorporated in a connection portion connected to the processor 200 or an operation unit operated by an operator. Incorporating the units in the connection portion would make it possible to avoid connection failure associated with connection.

Furthermore, according to an embodiment, the light source units 111 to 115 may be incorporated in the distal end portion of the electronic scope 100 where a light distribution lens 12 is provided. Incorporating the light source units 111 to 115 in the distal end portion enables omission of the LCB 11, leading to reduction of the diameter of the portion inserted into the body cavity, and reduction of the burden on the subject.

Figure 14:
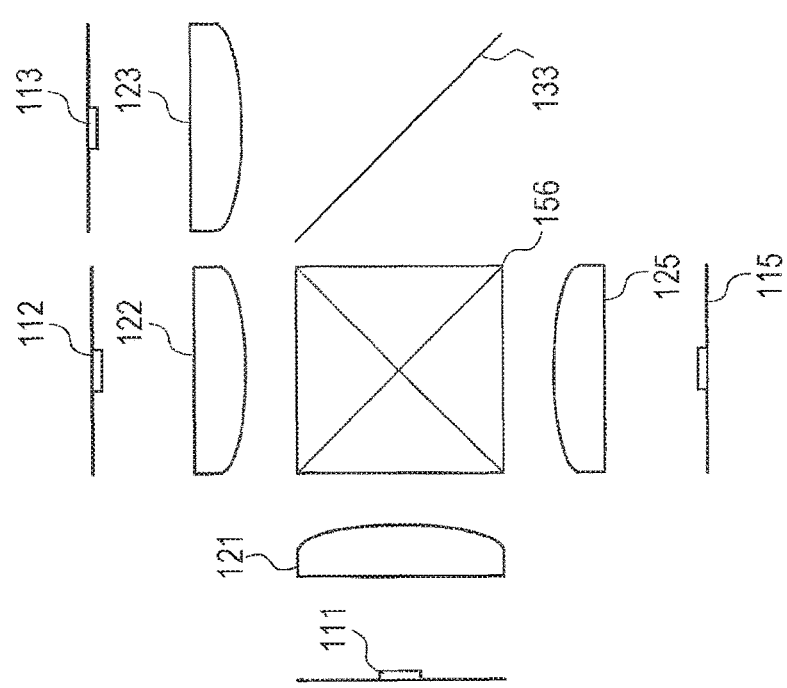
FIGS. 14(a) and 14(b) are diagrams illustrating an example of a configuration of an endoscope light source device according to another embodiment.
Figure 14:
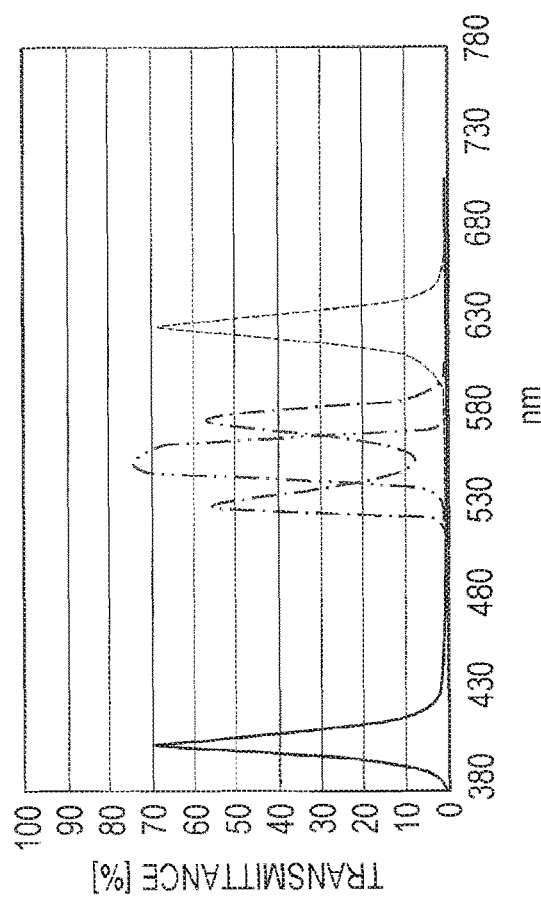

FIGS. 14(a) and 14(b) are diagrams illustrating an example of a configuration of an endoscope light source device according to another embodiment. FIG. 14(a) illustrates an example of an arrangement different from the arrangement of the light source units illustrated in FIGS. 13(a) and 13(b). FIG. 14(b) illustrates an example of a spectral distribution represented by the ratio of the light intensity of the light emitted by the arrangement of the light source unit illustrated in FIG. 14(a) to the light intensity at the outlet (transmittance of the optical element).

The light source unit, the optical element, and the collimating lens described below will be given the same reference numerals in a case where they are the same as the light source unit, the optical element, and the collimating lens illustrated in FIG. 5.

The arrangement illustrated in FIG. 14(a) is an arrangement of four light source units in which the four light source units 111, 112, 113, and 115 illustrated in FIG. 5 are used, and the light source unit 114 including a blue LED is not used. In this case, the light source units 111, 112, and 115 are disposed around an optical element 156. The light source unit 113 is provided downstream of the light emitted from the optical element 156, and the light emitted from the optical element 156 and a part of the light from the light source unit 113 are combined. The combined light can be emitted from the light distribution lens 127 as illumination light with a spectral waveform as illustrated in FIG. 14(b). For example, the combined light can be used as pseudo white light. In the optical elements 156 and 133, filter characteristics regarding removal and extraction of light are adjusted so as to generate a spectral waveform as illustrated in FIG. 14(b). Moreover, emitting light from only some of the light source units enables emission of a special ray of light. In the arrangement of the light source unit illustrated in FIG. 14(a), the optical element 156 is configured so as to receive incidence of light L112 from the light source unit 112 and generate emission light to be emitted toward the optical element 133 so as to allow the light to be transmitted light through the optical element 133. Therefore, overlapping the emission optical path of the transmitted light in the optical element 152 or the optical element 133 and the emission optical path of the reflected light in the optical element 152 or the optical element 133 makes it possible to easily generate the combined light in a wavelength band such as the special ray of light 2, obtained by combining the transmitted light and the reflected light, with a simple configuration.

Figure 15:
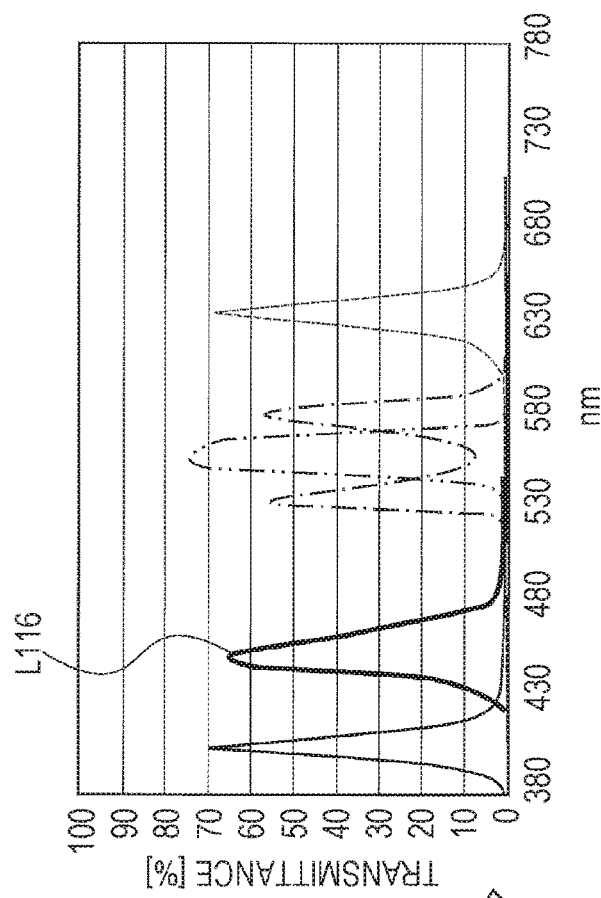
FIGS. 15(a) and 15(b) are diagrams illustrating an example of a configuration of an endoscope light source device according to another embodiment.
Figure 15:
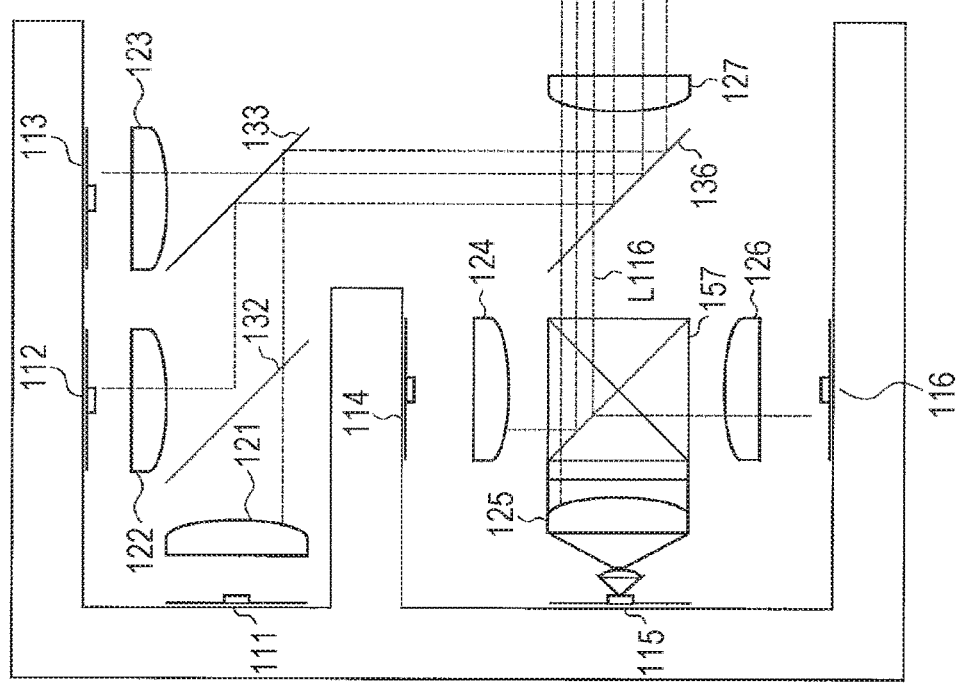

FIGS. 15(a) and 15(b) are diagrams illustrating an example of a configuration of an endoscope light source device according to another embodiment. FIG. 15(a) illustrates an example of an arrangement different from the arrangement of the light source units illustrated in FIG. 14(a). FIG. 15(b) is an example of a spectral distribution represented by the ratio of the light intensity of light emitted by the arrangement configuration of the light source unit illustrated in FIG. 15(a) to the light intensity at the outlet (transmittance of the optical element).

The arrangement illustrated in FIG. 15(a) is a six light source unit arrangement in which the four light source units 111, 112, 113, 114, and 115 illustrated in FIG. 5 are used, and the light source unit 116 that emits light having a peak wavelength of 530 nm in light intensity is used. A collimating lens 126 is provided on the front surface of the light source unit 116. In this case, the light source units 114 to 116 are arranged around an optical element 157. The light from the light source units 111 to 113 and the light from the light source units 114 to 116 are combined by the optical element 136. The combined light includes the light L116 from the light source unit 116. It is possible to emit light having a spectral waveform as illustrated in FIG. 15(b) from the light distribution lens 127 as illumination light. For example, the combined light can be used as pseudo white light. Moreover, emitting light from only some of the light source units enables emission of a special ray of light. For example, the special rays of light 1 and 2 can be generated by driving only the light source units 112 and 113 or driving only the light source unit 113 to emit light. In the optical elements 132, 133, 136, and 157, filter characteristics regarding removal and extraction of light are adjusted so as to generate a spectral waveform as illustrated in FIG. 15(b). In the arrangement of the light source unit illustrated in FIG. 15(a), the optical element 132 is configured so as to receive incidence of light L112 from the light source unit 112 and generate emission light to be emitted toward the optical element 133 so as to allow the light to be transmitted light at the optical element 133. Therefore, overlapping the emission optical path of the transmitted light in the optical element 133 and the emission optical path of the reflected light in the optical element 133 makes it possible to easily generate the combined light in the wavelength band such as the special ray of light 2, obtained by combining the transmitted light and the reflected light, with a simple configuration.

Figure 16:
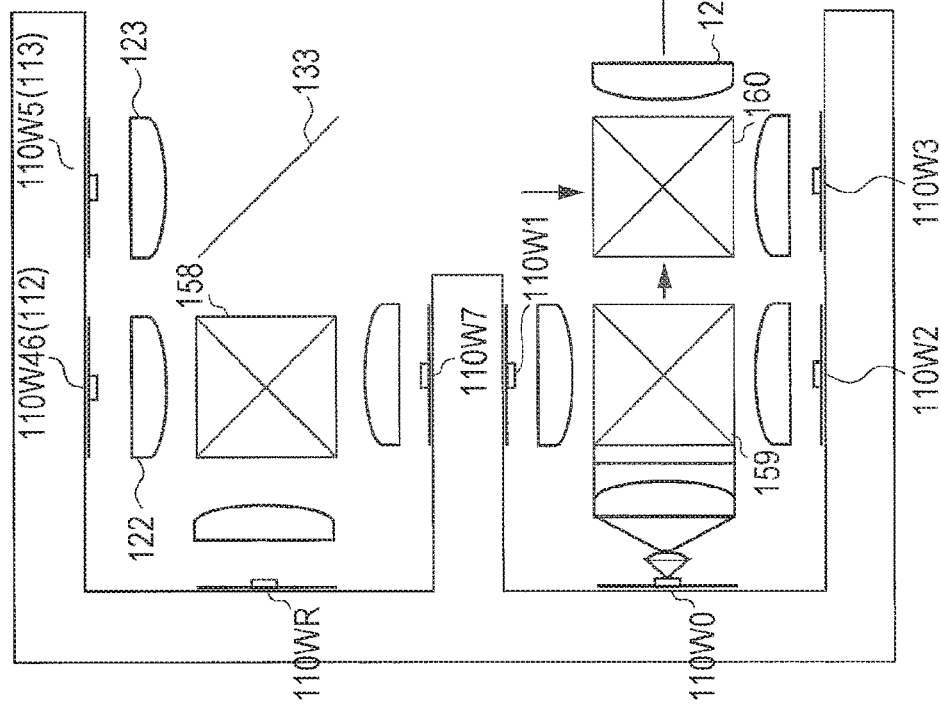
FIGS. 16(a) and 16(b) are diagrams illustrating an example of a configuration of an endoscope light source device according to another embodiment.
Figure 16:
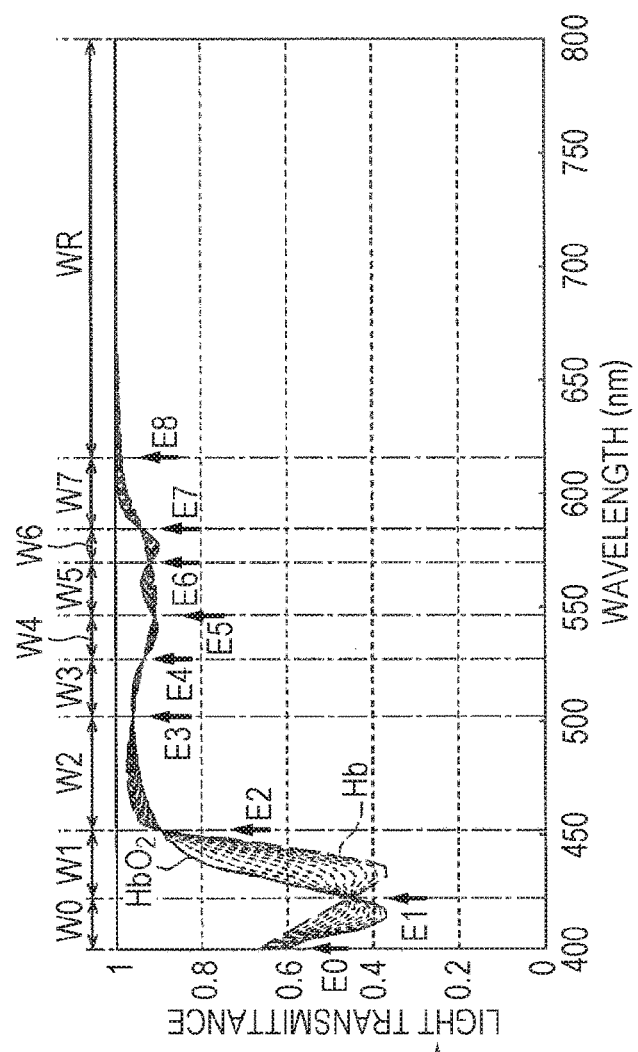

FIGS. 16(a) and 16(b) are diagrams illustrating an example of a configuration of an endoscope light source device according to an embodiment. FIG. 16(a) illustrates an example of an arrangement different from the arrangement of the light source units illustrated in FIG. 14(a). FIG. 16(b) is a diagram illustrating an example of a spectral waveform of a transmittance distribution generated by light absorption of hemoglobin. The arrangement illustrated in FIG. 16(a) is an arrangement in which eight light source units are used instead of the four light source units 111, 112, 113, 114, and 115 illustrated in FIG. 5.

A light source unit 110W0 emits light in a wavelength band including at least a wavelength band W0 having a wavelength of 400 nm to 422 nm illustrated in FIG. 16(b). A light source unit 110W1 emits light in a wavelength band including at least a wavelength band W1 having a wavelength of 422 nm to 452 nm illustrated in FIG. 16(b). A light source unit 110W2 emits light in a wavelength band including at least a wavelength band W2 having a wavelength of 452 nm to 502 nm illustrated in FIG. 16(b). A light source unit 110W3 emits light in a wavelength band including at least a wavelength band W3 having a wavelength of 502 nm to 526 nm illustrated in FIG. 16(b). Light source units 110W46 and 110W5 emit light in a wavelength band including at least wavelength bands W4 to W6 having a wavelength of 526 nm to 586 nm illustrated in FIG. 16(b). The light source units 110W46 and W5 emit substantially the same light as in the case of the light source unit 112 illustrated in FIG. 5. A light source unit 110W7 emits light in a wavelength band including at least a wavelength band W7 having a wavelength of 586 nm to 620 nm illustrated in FIG. 16(b). A light source unit 110WR emits light in a wavelength band including at least a wavelength band WR having a wavelength of 620 nm to 800 nm illustrated in FIG. 16(b). A collimating lens is provided on a front surface of each of these light source units.

The light source unit 110WR, the light source unit 110W46, and the light source unit 110W7 are provided around the optical element 158. The rays of light from these light source units are combined by the optical element 158 and emitted from the optical element 158. Subsequently the light emitted from the optical element 158 and the light from the light source unit 110W5 are combined by the optical element 133. The combined light emitted from the optical element 133 is emitted to the optical element 160. In the optical elements 158 and 133, the filter characteristics of light removal and extraction are adjusted so that light in the wavelength bands WR, W4 to W6, and W7 is to be emitted.

The light source unit 110W0, the light source unit 110W1, and the light source unit 110W2 are provided around the optical element 159, while the light source unit 110W3 is provided around the optical element 160. The rays of light from the light source unit 110W0, the light source unit 110W1, and the light source unit 110W2 are to be combined by the optical element 159 and emitted toward the optical element 160. The light emitted from the optical element 159, the light from the light source unit 110W3, and the combined light emitted from the optical element 133 are to be combined by the optical element 160. The combined light emitted from the optical element 160 is emitted from the light distribution lens 127 as illumination light. For example, the combined light can be used as pseudo white light. In the optical elements 159 and 160, filter characteristics of light removal and extraction are adjusted so that light in the wavelength bands WR and W0 to W7 is to be emitted.

Selecting any of these light source units and causing the selected unit to emit light makes it possible to generate special ray of light, for example, the special ray of lights 1 to 3 illustrated in FIGS. 10(b) to 10(d). In the arrangement of the light source unit illustrated in FIG. 16(a), the optical element 158 is configured to generate emission light to be emitted toward the optical element 133 so as to allow the light to be reflected light at the optical element 133, in response to the incidence of light L112 from the light source unit 110W46. Therefore, the emission optical path of the transmitted light in the optical element 133 and the emission optical path of the reflected light in the optical element 133 are configured to overlap with each other.

The waveform in solid line illustrated in FIG. 16(b) is a spectral waveform of the light transmittance of oxyhemoglobin (described as "HbO$_2$" in the figure), and the waveform in broken line is a spectral waveform of the light transmittance of deoxyhemoglobin (described as "Hb" in the figure). In this manner, the spectrum waveform of oxyhemoglobin and the spectral waveform of deoxyhemoglobin intersect at points E1 to E7. The spectrum waveform corresponding to the hemoglobin oxygen saturation always passes through the intersecting points E1 to E7, and is located between the spectral waveform of oxyhemoglobin and the spectrum waveform of deoxyhemoglobin. The higher the oxygen saturation, the closer the spectrum waveform is to the spectral waveform of oxyhemoglobin. The lower the oxygen saturation, the closer the spectrum waveform is to the spectrum waveform of deoxyhemoglobin. In the embodiment illustrated in FIGS. 2 to 5, the special rays of light 1 and 2 to calculate the oxygen saturation are used having the wavelength bands W4 to W6 as Wide-band (W-band) and the wavelength band W5 as Narrow-band (N-band), in FIG. 16(b). However, illuminating the biological tissue with light in one of the wavelength bands W0 to W7 would make it possible to obtain the level of oxygen saturation on the basis of the brightness level of the image produced by the degree of light absorption. Therefore, it is possible to illuminate a biological tissue with light in one of the wavelength bands W0 to W7 as special ray of light. Accordingly, a special ray of light can be obtained by emitting light from at least one of the light source unite W0 to W7, or by simultaneously emitting light from at least two of the light source unite W0 to W7. For example, light can be emitted simultaneously from the light source units W0, W2, W4, or the like to be used as a special ray of light, or light can be emitted simultaneously from the light source units W1, W3, W5, or the like to be used as the special ray of light.

The above has described the endoscope light source device and the endoscope system of the present invention in detail. The endoscope light source device and the endoscope system of the present invention are not limited to the above-described embodiment, and may of course be modified or altered in various ways in a range not deviating from the scope and spirit of the present invention.

REFERENCE SIGNS LIST

1 Endoscope system
11 LCB (Light Carrying Bundle)
12, 127 Light distribution lens
13 Objective lens
14 Solid-state image sensor
15 Driver signal processing circuit
16, 23 Memory
21 System controller
22 Timing controller
24 Operation panel
25 Condenser lens
26 Pre-stage signal processing circuit
27 Image memory
28 Poet-stage signal processing circuit
100 Electronic scope
111, 112, 113, 114, 115, 116, 110W0 to W7, 110WR Light source unit
112a, 113a Blue LED
112b, 113b Green phosphor
121 to 126 Collimating lens
132, 133, 134, 135, 150, 152, 154, 156, 157, 158, 159, 160 Optical element
140 Light source drive circuit
200 Processor
201 Light source device
300 Monitor

The invention claimed is:

1. An endoscope light source device configured to emit at least one of first light and second light of a wide second wavelength band including a first wavelength band of the first light,
the endoscope light source device comprising:
a first optical element configured such that first optical path incident light that is incident from a first optical path is changed to first optical path passing light by extracting a light component of the first wavelength band and removing light components other than the first wavelength band from the first optical path incident light, second optical path incident light that is incident from a second optical path of the optical element is changed to second optical path passing light by removing the light component of the first wavelength band and extracting the light components other than the light component of the first wavelength band from the second optical path incident light, and an emission optical path of the first optical path passing light and an emission optical path of the second optical path passing light are overlapped, and combined light of the first optical path passing light and the second optical path passing light that passes through the overlapped emission optical paths is to be emitted;
a first light source configured to emit first light source emission light that includes at least the light component of the first wavelength band and to allow the first light source emission light to be incident on the first optical element so that the first light source emission light is the first optical path incident light;
a second light source configured to emit second light source emission light that includes at least a light component of the second wavelength band and to allow light obtained from the second light source emission light, including at least the light component of the second wavelength band, to be the second optical path incident light of the first optical element;
a control unit configured to control on/off of emission of the first light source emission light and emission of the second light source emission light to perform emission of the first light and emission of the second light selectively,
wherein the control unit is configured to control the first light source emission light such that light intensity of the first light source emission light when the second light is emitted is different from the light intensity of the first light source emission light when the first light is emitted, so that a single peak wavelength of the second light is formed in intensity distribution;
the endoscope light source device further comprising a second optical element,
wherein the second light source emission light entering the second optical element is emitted to the first optical element from the second optical element, as the second optical path incident light of the first optical element;

the endoscope light source device further comprising a third light source configured to emit third light source emission light having a peak wavelength longer than a peak wavelength of the first light and the peak wavelength of the second light, toward the second optical element, wherein the second optical element is configured to emit combined light of the third light source emission light and light that includes at least a light component of the second wavelength band of the second light source emission light, to the first optical element in response to incidence of the third light source emission light and the second light source emission light; and the endoscope light source device further comprising:
a fourth light source configured to emit fourth light source emission light of a wavelength band having a peak wavelength shorter than the peak wavelength of the first light and the peak wavelength of the second light and including a wavelength of 415 nm; and
a third optical element configured to emit combined light of the fourth light source emission light and the emission light from the first optical element, as third light, in response to incidence of the fourth light source emission light and the emission light from the first optical element.

2. The endoscope light source device according to claim 1, wherein the control unit is configured to control driving of the first light source, the second light source, the third light source, and the fourth light source so as to repeatedly emit the first light, the second light, and the third light, as emission light.

3. An endoscope light source device configured to emit at least one of first light and second light of a wide second wavelength band including a first wavelength band of the first light, the endoscope light source device comprising:
a first optical element configured such that first optical path incident light that is incident from a first optical path is changed to first optical path passing light by extracting a light component of the first wavelength band and removing light components other than the first wavelength band from the first optical path incident light, second optical path incident light that is incident from a second optical path of the optical element is changed to second optical path passing light by removing the light component of the first wavelength band and extracting the light components other than the light component of the first wavelength band from the second optical path incident light, and an emission optical path of the first optical path passing light and an emission optical path of the second optical path passing light are overlapped, and combined light of the first optical path passing light and the second optical path passing light that passes through the overlapped emission optical paths is to be emitted;
a first light source configured to emit first light source emission light that includes at least the light component of the first wavelength band and to allow the first light source emission light to be incident on the first optical element so that the first light source emission light is the first optical path incident light;
a second light source configured to emit second light source emission light that includes at least a light component of the second wavelength band and to allow light obtained from the second light source emission light, including at least the light component of the second wavelength band, to be the second optical path incident light of the first optical element;

a control unit configured to control on/off of emission of the first light source emission light and emission of the second light source emission light to perform emission of the first light and emission of the second light selectively, wherein the control unit is configured to control the first light source emission light such that light intensity of the first light source emission light when the second light is emitted is different from the light intensity of the first light source emission light when the first light is emitted, so that a single peak wavelength of the second light is formed in intensity distribution;

the endoscope light source device further comprising a second optical element, wherein the second light source emission light entering the second optical element is emitted to the first optical element from the second optical element, as the second optical path incident light of the first optical element;

the endoscope light source device further comprising a third light source configured to emit third light source emission light having a peak wavelength longer than a peak wavelength of the first light and the peak wavelength of the second light, toward the second optical element, wherein the second optical element is configured to emit combined light of the third light source emission light and light that includes at least a light component of the second wavelength band of the second light source emission light, to the first optical element in response to incidence of the third light source emission light and the second light source emission light; and the endoscope light source device further comprising a fourth light source configured to emit fourth light source emission light of a wavelength band having a peak wavelength shorter than the peak wavelength of the first light and the peak wavelength of the second light and including a wavelength of 415 nm, wherein the second optical element is configured to emit combined light of the fourth light source emission light and light that includes at least a light component of the second wavelength band of the second light source emission light, to the first optical element in response to incidence of the fourth light source emission light and the second light source emission light.

4. An endoscope light source device configured to emit at least one of first light and second light of a wide second wavelength band including a first wavelength band of the first light, the endoscope light source device comprising:
a first optical element configured such that first optical path incident light that is incident from a first optical path is changed to first optical path passing light by extracting a light component of the first wavelength band and removing light components other than the first wavelength band from the first optical path incident light, second optical path incident light that is incident from a second optical path of the optical element is changed to second optical path passing light by removing the light component of the first wavelength band and extracting the light components other than the light component of the first wavelength band from the second optical path incident light, and an emission optical path of the first optical path passing light and an emission optical path of the second optical path passing light are overlapped, and combined light of the first optical path passing light and the second optical path passing light that passes through the overlapped emission optical paths is to be emitted;

a first light source configured to emit first light source emission light that includes at least the light component of the first wavelength band and to allow the first light source emission light to be incident on the first optical element so that the first light source emission light is the first optical path incident light;

a second light source configured to emit second light source emission light that includes at least a light component of the second wavelength band and to allow light obtained from the second light source emission light, including at least the light component of the second wavelength band, to be the second optical path incident light of the first optical element; and a control unit configured to control on/off of emission of the first light source emission light and emission of the second light source emission light to perform emission of the first light and emission of the second light selectively, wherein the second light source includes: a second solid-state light emitting element configured to emit second excitation light; and a second phosphor configured to emit second fluorescence by the second excitation light, wherein the second light source emission light includes the second excitation light and the second fluorescence, and wherein the second wavelength band is included in the wavelength band of the second fluorescence.

* * * * *